United States Patent [19]
Ishizaki et al.

[11] Patent Number: 5,981,070
[45] Date of Patent: Nov. 9, 1999

[54] WATER-ABSORBENT AGENT POWDERS AND MANUFACTURING METHOD OF THE SAME

[75] Inventors: Kunihiko Ishizaki, Suita; Kinya Nagasuna, Himeji; Nobuyuki Harada, Suita, all of Japan

[73] Assignee: Nippon Shokubai Co., Ltd, Osaka, Japan

[21] Appl. No.: 08/793,712

[22] PCT Filed: Jul. 5, 1996

[86] PCT No.: PCT/JP96/01863

§ 371 Date: Mar. 3, 1997

§ 102(e) Date: Mar. 3, 1997

[87] PCT Pub. No.: WO97/03114

PCT Pub. Date: Jan. 30, 1997

[30] Foreign Application Priority Data

Jul. 7, 1995 [JP] Japan .................................. 7-171895

[51] Int. Cl.$^6$ .................................. B32B 5/16; C08F 2/16
[52] U.S. Cl. .................. 428/407; 525/54.24; 525/54.26; 525/63; 524/800; 524/802; 524/804; 524/812; 521/53; 521/55; 521/57; 521/905; 428/403; 428/407
[58] Field of Search .............................. 525/54.24, 54.26, 525/63; 524/800, 802, 804, 812; 521/53, 55, 57, 905; 428/403, 407

[56] References Cited

U.S. PATENT DOCUMENTS

| | | | |
|---|---|---|---|
| 4,666,983 | 5/1987 | Tsubakimoto et al. | 525/119 |
| 4,794,166 | 12/1988 | Engelhardt et al. | 528/492 |
| 5,229,488 | 7/1993 | Nagasuna et al. | 528/487 |
| 5,322,896 | 6/1994 | Ueda et al. | 525/119 |
| 5,369,148 | 11/1994 | Takahashi et al. | 523/315 |
| 5,382,610 | 1/1995 | Harada et al. | 524/35 |
| 5,399,591 | 3/1995 | Smith et al. | 521/53 |

FOREIGN PATENT DOCUMENTS

| | | |
|---|---|---|
| 0 668 080 A2 | 8/1995 | European Pat. Off. . |
| 63-61005 | 3/1988 | Japan . |
| 2-132103 | 5/1990 | Japan . |
| 3-195705 | 8/1991 | Japan . |
| 4-87638 | 3/1992 | Japan . |
| 4-501877 | 4/1992 | Japan . |
| 6-200046 | 7/1994 | Japan . |
| 7-224204 | 8/1995 | Japan . |

*Primary Examiner*—Samuel A. Acquah
*Attorney, Agent, or Firm*—Kubovcik & Kubovcik

[57] ABSTRACT

A manufacturing method of water-absorbent agent powders of the present invention is a method of a reducing an amount of a residue of an epoxy crosslinking agent remaining therein by adding a nucleophilic reagent in a form of powder to surface region crosslinked water-absorbent resin powders having a carboxyl group under an applied heat in which the residue of the crosslinking agent remains. Since the method permits an amount of the residue of the crosslinking agent to be reduced by adding a nucleophilic reagent to the heated water-absorbent resin powders, the water-absorbent agent powders exhibiting well-balanced properties which are mutually negatively correlated from one another, i.e., high absorbency under pressure, a reduced amount of a residue of the epoxy crosslinking agent and a high absorbing rate compared with the conventional surface region crosslinked water-absorbent resin powders can be achieved. Such water-absorbent agent powders are suitably used in sanitary materials such as disposable diaper, sanitary napkins, etc.

43 Claims, 3 Drawing Sheets

WATER-ABSORBENT AGENT POWDERS AND MANUFACTURING METHOD OF THE SAME

FIELD OF THE INVENTION

The present invention relates to water-absorbent agent powders and a manufacturing method of the same, and more particularly to water-absorbent agent powders befitting sanitary materials, which manifest as high an absorbency under pressure as without pressure, excel in safety as evinced by the absence of a residue of a cross-linking agent in the resin, while manifesting a high absorbing rate, and also relates to a manufacturing method of the same.

BACKGROUND OF THE INVENTION

In recent years, a water-absorbent resin is widely used in sanitary goods such as disposable diapers, sanitary napkins, etc., for the purpose of absorbing and holding body fluid such as urine, blood, etc., to prevent clothes from being contaminated.

Examples of the conventionally known water-absorbent resins may be but are not limited to:

a partially neutralized crosslinked polymer of polyacrylic acid (Japanese Unexamined Patent Publication No. 84304/1980 (Tokukaisho 55-84304), Japanese Unexamined Patent Publication No. 108407/1980 (Tokukaisho 55-108407) and Japanese Unexamined Patent Publication No. 133413/1980 (Tokukaisho 55-133413));

a hydrolyzed graft polymer of starch-acrylonitrile (Japanese Examined Patent Publication No. 43995/1971 (Tokukosho 46-43995));

a neutralized graft polymer of starch-acrylic acid (Japanese Unexamined Patent Publication No. 125468/1976 (Tokukaisho 51-125468));

a saponified copolymer of vinyl acetate-acrylic ester (Japanese Unexamined Patent Publication No. 14689/1977 (Tokukaisho 52-14689));

cross-linked carboxymethyl cellulose (U.S. Pat. No. 4,650,716 and U.S. Pat. No. 4,689,408);

a hydrolyzed copolymer of acrylonitrile or of acrylamide, or a cross-linked copolymer of both (Japanese Unexamined Patent Publication No. 15959/1978 (Tokukaisho 53-15959));

a crosslinked polymer of cationic monomer (Japanese Unexamined Patent Publication No. 154709/1983 (Tokukaisho 58-154709) and Japanese Unexamined Patent Publication No. 154710/1983 (Tokukaisho 58-154710));

cross-linked isobutylene-maleic anhydrous copolymers (U.S. Pat. No. 4,389,513); and cross-linked copolymers of 2-acryl-amide-2-methylpropanesulfonic acid with acrylic acid (EP068189).

The properties which the water-absorbent resins are desired to possess include, for example, high absorbency and high absorbing rate to be manifested on contact with aqueous liquids, liquid permeability, high strength exhibited by the gel swollen with liquid, and ability to aspirate water from the substrate impregnated with aqueous liquid, less residue of monomer (U.S. Pat. No. 4,794,166).

These properties are not necessarily correlated positively to one another, and a problem arises, for example, in that such properties as the liquid permeability, the gel strength, and the absorbing rate are lowered in proportion as the absorbency is heightened.

As a means to improve the various water-absorbent properties of the water-absorbent resin in finely balanced levels, the technique of cross-linking the surface regions of the water-absorbent resin has been known. Various methods have been proposed concerning the technique.

For example, a method using polyhydric alcohols (Japanese Unexamined Patent Application No. 108233/1983 (Tokukaisho 58-108233), and Japanese Unexamined Patent Application No. 16903/1986 (Tokukaisho 61-16903)), a method using polyglycidyl compounds, poly aziridine compounds, polyamine compounds, and polyisocyanate compounds (Japanese Unexamined Patent Application No. 189103/1984 (Tokukaisho 59-189103) and (U.S. Pat. No. 4,666,893)), methods using glyoxal (Japanese Unexamined Patent Application No. 117393/1977 (Tokukaisho 52-117393)), methods using polyvalent metals (Japanese Unexamined Patent Application No. 136588/1976 (Tokukaisho 51-136588), Japanese Unexamined Patent Application No. 257235/1986 (Tokukaisho 61-257235) and Japanese Unexamined Patent Application No. 7745/1987 (Tokukaisho 62-7745)), methods using a silane coupling agent (Japanese Unexamined Patent Application No. 211305/1986 (Tokukaisho 61-211305), Japanese Unexamined Patent Application No. 252212/1986 (Tokukaisho 61-252212) and Japanese Unexamined Patent Application No. 264006/1986 (Tokukaisho 61-264006)), a method using a monoepoxy compound (Japanese Unexamined Patent Application No. 87638/1992 (Tokukaihei 4-87638)), a method using a polymeric compound having an epoxy group (U.S. Pat. No. 4,758,617), a method using an epoxy compound and a hydroxy compound (Japanese Unexamined Patent Application No. 132103/1990 (Tokukaihei 2-132103)), and a method using an alkylene carbonate (DE-4020780) have been known.

Other than the described methods, methods requiring the presence of an inorganic inactive powder (Japanese Unexamined Patent Application No. 163956/1985 (Tokukaisho 60-163956) and Japanese Unexamined Patent Application No. 255814/1985 (Tokukaisho 60-255814)), a method requiring the presence of a dihydric alcohol (Japanese Unexamined Patent Application No. 292004/1989 (Tokukaihei 1-292004)), a method requiring the presence of water and an ether compound (Japanese Unexamined Patent Application No. 153903/1990 (Tokukaihei 2-153903)), a method requiring the presence of a water-soluble polymer (Japanese Unexamined Patent Application No. 126730/1991 (Tokukaihei 3-126730)), and a method requiring the presence of the alkylene oxide additive of a monohydric alcohol, an organic acid salt, lactam, etc. (EP-0555692, and U.S. Pat. No. 5,322,896), a method of mixing a surface crosslinking agent with heated water-absorbent resin in which not less than 90 percent of particles have a size of not less than 250 $\mu$m (Japanese Unexamined Patent Application No. 224204/1995 (Tokukaihei 7-224204)) and a method of mixing a reducing agent with a surface crosslinking agent (U.S. Pat. No. 5,382,610) have been known.

Also, to attain improved properties of surface region crosslinked particles, a method of granulating the particles with an aqueous solution (U.S. Pat. No. 5,369,148), and a method of adding a cationic polymer having a molecular weight of not less than 2,000 in order to be fixed with the fiber material (U.S. Pat. No. 5,3282,610) have been known.

Further, EP-668080 published on Aug. 23, 1995 discloses a method in which a surface crosslinkage is carried out by adding organic acid/inorganic acid/polyamino acid.

The described methods permit some improvements in a balance of various properties of the water-absorbent resin, yet further improvements are needed to reach a desirable level. This has led to the need for further developments to attain improved properties of the water-absorbent resin.

In recent years, such a water-absorbent resin that excels in basic water-absorbent properties under pressure, especially in absorbency under pressure, while maintaining as high absorbency without pressure as the conventional water-absorbent resin has been strongly demanded.

Specifically, the demand for the water-absorbent resin which excels in absorbency under high pressure (for example, under load of 50 g/cm$^2$) and exhibits high absorbency even under heavy load has been increasing. Here, a heavy load is defined to be a load incurred when not only a baby weighing around 10 Kg but also an adult person uses a sanitary material including a water-absorbent resin.

To meet the described needs, an improvement in crosslinkage to be applied to the surface regions of the water-absorbent resin are essential. To be specific, in order to meet the demands, it is required to increase the degree of crosslinkage of the surface regions. To do so, an amount of use of the surface crosslinking agent is increased or in order to uniformly crosslink only the surface regions, an amount of water or solvent to be added with the crosslinking agent is reduced.

However, in such cases, the crosslinking agent is likely to remain on the surface of the resin. Such problems do not occur when adopting a crosslinking agent that has low reactivity and excels in safety such as polyhydric alcohol, etc.

However, in the case of adopting the crosslinking agent of high reactivity such as epoxy compound, etc., it is likely that surface regions are crosslinked immediately, and excellent properties are likely to be obtained. On the other hand, however, the surface crosslinking agent itself is acrid to skin. Thus, when a large amount of the crosslinking agent is contained in the water-absorbent resin, a new problem is raised in its safety when applying it to sanitary materials. Namely, in the conventional water-absorbent resins, an epoxy compound remains in an order of from several tens to 1,000 ppm.

In order to reduce an amount of a residue in the resin of the crosslinking agent for crosslinking the surface regions, the surface regions of the water containing gel-like resin at a specific water content ranging from 10 to 30 percent, a method of further adding a predetermined amount of water during the process is known (Japanese Unexamined Patent Application No. 195705/1991 (Tokukaihei 3-195705)).

Such method necessitates complicated processes, and the surface crosslinking agent is penetrated to the inside of the particles because of its high water content. As a result, the absorbency under high pressure as well as without pressure is lowered to an insufficient level, and a significant effect of reducing the amount of a residue of the crosslinking agent cannot be expected. Namely, the inventors of the present invention have found that these properties are negatively correlated to one another.

In order to meet a demand for thinner diapers of higher performances, there is a tendency of reducing a fiber material such as pulp from the water-absorbent material and increasing an amount of the water-absorbent resin, i.e., increasing the density of the water-absorbent resin. However, when the density is increase in a diaper, as the water-absorbent resin has a lower absorbing rate as compared with pulp, it is required to improve the absorbing rate of the water-absorbent resin.

In order to ensure high absorbing rate of the water-absorbent resin, it is required to increase a surface area of the water-absorbent resin. However, if the absorbing rate is increased merely by reducing a particle diameter, liquid permeability is lowered. To avoid such problem, the surface area is increased without reducing the particle diameter, for example, by pulverizing the water-absorbent resin to be crushed in an irregular shape, or foaming the water-absorbent resin.

Further, a method of crosslinking the surface of foamed and porous water-absorbent resin to improve the absorbing rate and the absorbency under pressure (U.S. Pat. No. 5,399,591) is also known.

However, in the case of increasing the absorbency under high pressure by carrying out a surface crosslinkage of the foamed porous water-absorbent resin, due to its wide surface area, it is required to add the surface crosslinking agent in a still greater amount, and it is difficult to uniformly add the surface crosslinking agent to particles. As a result, it has been found that the amount of a residue of the surface crosslinking agent is increased. Namely, it has been found that an improvement in absorbing rate, which has been strongly demanded among the properties of the water-absorbent resin, and a reduction in amount of a residue of the surface crosslinking agent are negatively correlated to one another.

In order to obtain absorbency under high pressure, in general, the amount of the surface crosslinking agent is increased from the conventional method as described above. However, in such case, as the crosslinking density of the surface regions is too high, the absorbing rate is reduced on the contrary.

Namely, it is well known in the art that the absorbing rate is increased by the surface crosslinkage. However, it has been found that when surface crosslinkage is carried out to sufficiently increase the absorbency under high pressure (for example 50 g/cm$^2$) to be durable even against heavier weight, the absorbing rate defined in the present invention is lowered compared with the water-absorbent resin before the surface crosslinkage. Namely, it has been found that an improvement in absorbency under high pressure and an improvement in absorbing rate may be negatively correlated to one another.

As described, the inventors of the present invention have raised new problems that: (1) an improvement in absorbency under high pressure durable for heavy weight and a reduction in an amount of a residue of the epoxy crosslinking agent may be negatively correlated, (2) an improvement in absorbing rate by the area/weight ratio and a reduction in an amount of a residue of the epoxy crosslinking agent may be negatively correlated and (3) an improvement in absorbency under high pressure, and an improvement in absorbing rate may be negatively correlated.

Accordingly, an object of the present invention is to provide new absorbent agent powders which exhibit an improvement in absorbency under high pressure, a reduction in an amount of a residue of the epoxy crosslinking agent and an improvement in absorbing rate, and the manufacturing method of the same.

DISCLOSURE OF INVENTION

Earnest researches have been made to accomplish the above object. As a result, the inventors of the present invention have found that by processing with a specific compound, a water-absorbent resin having a carboxyl group whose surface regions are denatured by the crosslinking agent having an epoxy group and in which the crosslinking agent remains as a residue, water-absorbent agent powders which exhibit high absorbing rate and a reduced amount of a residue of the crosslinking agent while maintaining various water-absorbent properties such as high absorbency under high pressure, etc., with can be obtained.

The manufacturing method of the water-absorbent agent powders of the present invention is characterized in that a nucleophilic reagent is added to heated water-absorbent resin powders having a carboxyl group in a form of a powder, whose surface regions are crosslinked by a crosslinking agent having an epoxy group, in which the crosslinking agent remaining as a residue is reduced.

Another manufacturing method of the water-absorbent agent powders of the present invention is characterized in that water-absorbent resin powders having a carboxyl group, in which surface regions are crosslinked by a crosslinking agent having an epoxy group and in which the crosslinking agent remains therein is washed so as to reduce the amount of the residue of the crosslinking agent.

A still another manufacturing method of water-absorbent agent powders of the present invention is characterized as comprising the step of:

adding at least one member selected from the group consisting of a water-soluble surface active agent and a water-soluble polymer to dried water-absorbent resin powders of an irregular crushed shape having a carboxyl group, whose surface regions are crosslinked, in a sufficient amount for increasing an absorbing rate (g/g/sec) of the water-absorbent resin powders defined based on 28 times swelling time with artificial urine above an absorbing rate of the surface crosslinked water-absorbent resin powders, said water-absorbent resin powders having an absorbency under pressure based on the physiologic saline solution under load of 50 g/cm² increased to at least 20 g/g.

Yet still another method of manufacturing water-absorbent resin powders of the present invention is characterized by including the step of adding water to at least partially porous water-absorbent resin powders having a carboxyl group, and the water-absorbent resin powders being surface crosslinked by a crosslinking agent having an epoxy group and containing a residual surface crosslinking agent having the epoxy group so as to have an absorbency under pressure of not less than 20 g/g based on a physiologic saline solution under load of 50 g/cm², whereby an amount of the residue of the crosslinking agent of the mixture is reduced.

The water-absorbent agent powders of the present invention are at least partially porous water-absorbent resin powders, in which surface regions of the water-absorbent resin powders are crosslinked by a crosslinking agent having an epoxy group, and an amount of the residue of the crosslinking agent is not more than 2 ppm.

The following will describe the present invention in detail.

The water-absorbent resin of the present invention is the water-absorbent resin powders having a carboxyl group in which surface regions are crosslinked by a crosslinking agent having an epoxy group, and the crosslinking agent remains therein.

It is preferable that the water-absorbent resin powders have an absorbency under pressure based on a physiologic saline solution under load of 50 g/cm² of not less than 20 g/g and more preferably not less than 25 g/g.

From the viewpoint of absorbing rate, the water-absorbent resin powders of an irregular crushed shape having a large specific surface area, and preferably water-absorbent resin powders in which at least a part of the particles is porous, having a specific surface area based on the particles in size ranging from around 300 to 600 µm before the surface crosslinkage being less than 0.025 m²/g. It is preferable that the water content of the water-absorbent resin powders is less than 10 percent, more preferably less than 5 percent.

For example, such water-absorbent resin powders can be obtained by crosslinking the surface regions of a hydrophilic cross-linked polymer as a resin precursor by the crosslinking agent having an epoxy group under a specific condition. However, the water-absorbent resin powders having a carboxyl group in which the crosslinking agent does not remain in the resin shows low absorbency under high pressure, and such resin is not suited for the present invention.

In the present invention, the amount of a residue of the crosslinking agent having an epoxy group in the water-absorbent resin powders is required to be not less than a predetermined amount in order to increase the absorbency under high pressure. It is preferable that the predetermined value is above 2 ppm, more preferably not less than 5 ppm and still more preferably not less than 10 ppm.

The upper limit of the amount of a residue of the crosslinking agent having an epoxy group is not particularly limited in the present invention. However, it is not efficient to have a residue in an excessive amount of the crosslinking agent because more than a certain level of the absorbency under pressure would not be obtained, and a longer time and a larger amount of the nucleophilic reagent would be required for reducing the amount of the residue of the crosslinking agent. In consideration of the above, it is preferable that an upper limit amount of the residue is not more than 2,000 ppm, more preferably not more than 1,000 ppm, and still more preferably not more than 500 ppm. Namely, in order to obtain high grade properties and a significant reduction in the amount of a residue of the surface crosslinking agent, it is preferable that the amount of a residue of the crosslinking agent is in a range of from 2 ppm to 2,000 ppm, more preferably from 3 to 1,000 ppm and still more preferably from 4 to 500 ppm.

Hereinafter, a water-absorbent polymer which is not surface crosslinked is defined to be the hydrophilic crosslinked polymer or the resin precursor, a hydrophilic crosslinked polymer or the surface crosslinked resin precursor which is surface crosslinked is defined to be water-absorbent resin, and further the water-absorbent resin to which the process of the present invention is applied is defined to be water-absorbent agent powders.

The water-absorbent resin powders of the present invention is obtained by mixing an aqueous solution in an amount of from 0.005 part by weight to 2 parts by weight of a crosslinking agent having an epoxy group, more preferably from 0.02 part by weight to 1.5 parts by weight, still more preferably from 0.06 part by weight to 1 part by weight, and from 0.1 part by weight to 10 parts by weight of water based on 100 parts by weight of the resin precursor before surface regions are crosslinked although a suitable amount of the aqueous solution differs depending on a surface area of the resin precursor, i.e., the grain size and shape of the resin precursor powder and presence or absence of foams.

By controlling the respective amounts of the crosslinking agent having an epoxy group and the aqueous solution with respect to the resin precursor in a specific range, the resulting water-absorbent resin powders show high absorbency under high pressure in which a residue of the crosslinking agent having an epoxy group remains, which are suited for use in the present invention.

Under the described control, the water-absorbent resin powders of the present invention show high absorbency under high pressure and contain a residue of the crosslinking agent having an epoxy group and have a carboxyl group.

The water-absorbent resin powders become the water-absorbent agent powders of the present invention having high absorbency under high pressure, and less residue of the cross-linking agent having an epoxy group, by applying the process of the present invention.

In the present invention, in order to improve properties and reduce an amount of a residue of the crosslinking agent, for the aqueous solution containing the crosslinking agent, a combined use of organic hydrophilic solvent and water is adopted as the aqueous solution containing a crosslinking agent. Examples of such hydrophilic organic solvent may be but are not limited to: lower alcohols, such as methyl alcohol, ethyl alcohol, n-propyl alcohol, isopropyl alcohol, n-butyl alcohol, isobutyl alcohol, and t-butyl alcohol;

ketones, such as acetone;

ethers, such as dioxane, tetrahydrofuran, alkoxypolyethylene glycol;

amides, such as N,N-dimethylformamide;

sulfoxides, such as dimethylsulfoxide; etc.

In the present invention, the amount of use of such hydrophilic organic solvent is in a range of from 0 to 10 parts by weight, preferably less than 5 parts by weight with respect to 100 parts by weight of the solid portion of the resin precursor.

The resin precursor to be used in the present invention is not particularly limited, and any resin precursor having a carboxyl group may be used. For example, a hydrophilic crosslinked polymer which forms substantially water-insoluble hydrogel swollen with a large amount of water, preferably swollen with from 10 to 100 times by weight of a physiologic saline solution without pressure may be used. The crosslinked polymer is such as a partially neutralized polyacrylic acid salt crosslinked polymer, a graft polymer of starch-acrylic acid, crosslinked carboxymethyl cellulose, etc.

The substantially water-insoluble hydrogel is defined to be those having a solubility of the absorbent resin in excessive amount of pure water, i.e., the content of extractables is not more than 50 percent by weight, preferably not more than 20 percent by weight and still more preferably not more than 10 percent by weight.

For the resin precursor in the present invention, a hydrophilic crosslinked polymer resulting from polymerizing a hydrophilic aqueous monomer containing acrylic acid and/or a salt thereof as main components in a presence of the crosslinking agent or grafted main chain is suitably and typically used.

Examples of the salt of acrylic acid may be but are not limited to: alkali metal salt of acrylic acid, ammonium salt of acrylic acid, amine salt of acrylic acid, etc. Among them, alkali metal salt is preferable, and sodium salt is still more preferable.

For the unit structure of the polymer, that having from 40 to 100 mole percent, preferably from 50 to 95 mole percent and still more preferably from 60 to 90 mole percent neutralized carboxyl group obtained from acrylic acid is preferable. The neutralization may be carried out with respect to the monomer before polymerization, or hydrogel polymer during or after polymerization.

When the water-absorbent resin is obtained by polymerizing a hydrophilic monomer having acrylic acid and/or a salt thereof as a main component thereof, for example, with a combined use of acrylic acid and or salts thereof, other monomers may be copolymerized if necessary. The method of manufacturing acrylate salt suited for use in the polymerization of the hydrophilic crosslinked polymer is exemplified in U.S. Pat. No. 5,338,819 and EP Patent No. 0574260.

Examples of the monomer usable for the copolymerization, other than acrylic acid, may be but are not limited to:

anionically unsaturated monomers such as methacrylic acid, maleic acid, β-acryloyloxy propionic acid, vinyl sulfonic acid, styrene sulfonic acid, 2-(meth)acrylamide-2-methyl propanesulfonic acid, 2-(meth)acryloyl ethanesulfonic acid, and 2-(meth)acryloyl propanesulfonic acid and salts thereof;

nonionic hydrophilic group-containing unsaturated monomers such as acrylamide, methacrylamide, N-ethyl(meth)acrylamide, N-n-propyl(meth)acrylate, N-isopropyl(meth)acrylamide, N,N-dimethyl(meth)acrylamide, 2-hydroxyethyl(meth)acrylate, 2-hydroxypropyl (meth)acrylate, methoxypolyethylene glycol (meth)acrylate, polyethyleneglycol mono(meth)acrylate, vinylpyridine, N-vinyl pyrrolidone, N-acryloylpiperidine, and N-acryloyl pyrrolidine; and cationically unsaturated monomers such as N,N-dimethylaminoethyl (meth)acrylate, N,N-diethylaminoethyl (meth)acrylate, N,N-dimethyl aminopropyl (meth)acrylate, N,N-dimethylaminopropyl (meth)acrylamide, and quaternary salts thereof.

It is also permitted to use hydrophobic unsaturated monomer such as isobutylene, stearyl (meth)acrylate, etc., as long as the water-absorbent properties are not adversely affected. The amount of other monomer is generally in the range of from 0 to 50 mol percent, preferably from 0 to 30 mol percent, most preferably from 0 to 10 mol percent, based on the amount of all the component monomers for the copolymerization.

As the water-absorbent resin for use in this invention, although it has a cross-linking structure, the water-absorbent resin obtained by the copolymerization or the reaction using an inner crosslinking agent having not less than two polymerizing unsaturated groups or not less than two reacting groups or both of polymerizing unsaturated group and reactive group is more preferable than the water-absorbent resin of the self-crosslinkable type which has no use for the crosslinking agent.

Examples of the inner cross-linking agent may be but are not limited to:

N,N'-methylene-bis (meth)acrylamide, (poly) ethyleneglycol di (meth) acrylate, (poly) propylene glycoldi(meth)acrylate, trimethylol-propane tri(meth)acrylate, trimethylol-propane di(meth) acrylate, glycerol tri(meth)acrylate, glycerol acrylate methacrylate, ethyleneoxidemodified trimethylolpropane tri(meth)acrylate, pentaerythritol tetra(meth)acrylate, dipentaerythritol hexa (meth)acrylate, triallyl cyanurate, triallyl isocyanurate, triallyl phosphate, triallyl amine, poly(meth)allyloxyalkane, (poly)ethyleneglycol diglycidyl ether, glycerol diglycidyl ether, ethylene glycol, polyethyleneglycol, propyleneglycol, glycerol, pentaerythritol, ethylenediamine, polyethyleneimine, and glycidyl (meth)acrylate. These inner cross-linking agents, when necessary, may be used in the form of a combination of two or more members.

From the viewpoint of the water-absorbent properties of the produced water-absorbent resin, it is particularly preferable to use essentially a compound having not less than two polymerizable unsaturated groups as an inner cross-linking agent. The amount of the inner cross-linking agent to be used is preferably in the range of from 0.005 to 2 mole percent, more preferably from 0.01 to 1 mole percent to the monomers.

The monomers to be polymerized may incorporate therein a hydrophilic polymeric compound such as starch or cellulose, starch derivatives or cellulose derivatives, polyvinyl alcohol, polyacrylic acid (polyacrylate salt) or crosslinked polyacrylic acid (polyacrylate salt), a chain transfer agent such as hypophosphorous acid (salt), surfactants, and foaming agents such as carbonates, etc.

The compounds for addition to these monomers are disclosed in U.S. Pat. No. 4,076,663, U.S. Pat. No. 4,286,082, U.S. Pat. No. 4,320,040, U.S. Pat. No. 4,833,222, U.S. Pat. No. 5,118,719, U.S. Pat. No. 5,149,750, U.S. Pat. No. 5,154,713, U.S. Pat. No. 5,264,495, EP No. 03729831, and EP No. 0496594.

In the polymerization of the monomer for the production of the water-absorbent resin for use in the present invention, though bulk polymerization or precipitation polymerization is available, it is preferable to prepare the monomer in the form of an aqueous solution and subject the aqueous solution to a solution polymerization or reversed-phase suspension polymerization from the viewpoint of the quality of product and the ease of control of polymerization. Examples of the solution polymerization may be but are not limited to: a casting polymerization to be carried out within a mold, a thin layer polymerization to be carried out by placing thinly on a belt conveyer, a polymerization to be carried out by dividing the resulting hydrogel polymer into fine pieces, etc.

When carrying out the solution polymerization, the concentration of the aqueous solution is in the range of from 10 to 70 percent by weight, preferably from 20 percent by weight to a saturated concentration. Further, both continuous-type and batch-type polymerizations can be adopted for such solution polymerization, and under any of reduced pressure, applied pressure, or atmospheric pressure. In general, it is further preferable that the polymerization is carried out in an inactive air flow such as nitrogen, helium, argon, carbon dioxide gas, etc.

When carrying out the polymerization, for example, known polymerization methods such as a polymerization using a radical polymerization initiator, an irradiation polymerization, an electron beam polymerization, an ultraviolet ray polymerization by a photosensitizer, etc., may be adopted; however, in order to carry out a polymerization quantitatively and completely, it is preferable to adopt a polymerization by a radical polymerization initiator. Examples of the radical polymerization are: a reverse-phase suspension polymerization (U.S. Pat. Nos. 4,093,776, 4,367,323, 4,446,261, 4,683,274, 4,973,632); and solution polymerization (U.S. Pat. Nos. 4,552,938, 4,625,001, 4,654,393, 4,703,067, 4,873,299, 4,985,514, 5,124,416, 5,250,640).

To initiate a polymerization, for example, a radical polymerization initiator such as potassium persulfate, ammonium persulfate, sodium persulfate, t-butylhydroperoxide, hydrogenperoxide, 2,2'-azobis(2-amidinopropane) dihydrochloride, etc., or an active energy ray, such as an ultraviolet ray, an electron beam, etc., may be used. However, it is preferable to adopt the radical polymerization initiator.

In the case of employing an oxidative radical polymerization initiator, a redox polymerization may be carried out with a combined use of a reducing agent such as sodium sulfite, sodium hydrogen sulfite, ferrous sulfate, formamidine sulphinic acid, L-ascorbic acid (salt), etc. It is permitted to use more than one kind of such polymerization initiators and the reducing agents, and the amount of use thereof is preferably in the range of from 0.001 to 2 mole percent, more preferably in the range of from 0.01 to 0.5 mole percent to the monomers.

In the case of polymerizing a monomer component by the solution polymerization, it is preferable to dry the resulting gel-like polymer by a known drying method such as a hot-air drying method, a drying method under specific moisture (U.S. Pat. No. 4,920,202), a microwave drying method (U.S. Pat. No. 5,075,344), drying method under reduced pressure, a drying method using a drum dryer, or an azeotropic dehydration in a hydrophobic organic solution.

The drying temperature preferably ranges from 70 to 300° C., more preferably from 100 to 250° C., and more preferably from 150 to 200° C. Prior to applying the drying treatment, water-absorbent resin fine powders may be recycled into a gel-like polymer, and ground by the method disclosed in U.S. Pat. No. 5,064,582 and U.S. Pat. No. 5,478,879, or the polymer in the form of gel may be cut into fine pieces by the method disclosed in U.S. Pat. No. 5,275,773, or a supply of the polymer in the form of gel to the dryer may be controlled by the method disclosed in U.S. Pat. No. 5,229,487.

The resulting hydrophilic crosslinked polymer in the present invention as a resin precursor from the described polymerization preferably has an irregular crushed shape, spherical, fiber, or sheet. In the case of having substantially spherical shape, the polymer is preferably obtained by a reverse phase suspension. However, to maximize the effects of the present invention, i.e., to obtain excellent water-absorbent agent powders which show high absorbency both under pressure and without pressure, excel in safety as evinced by the absence of a residue of a cross-linking agent, it is preferable to use spherical or irregular crushed shape as a raw material.

From the viewpoint of high absorbing rate evinced by a high specific surface area, and fixability to pulp, it is preferable to use a hydrophilic crosslinked polymer of irregular crushed shape resulting essentially from carrying out a solution polymerization and subsequent pulverization, and more preferably at least a partially porous hydrophilic crosslinked polymer of irregular crushed shape as the resin precursor. Further, whether the porosity is of an open cell or closed cell is not specified.

In the present invention, at least partially porous particle is defined such that existence and absence of pores in a plurality of particles is observable in a from 30 to 100 times enlarged electron micrograph. In the present invention, not less than 2 percent, preferably not less than 5 percent and still more preferably not less than 10 percent particles are porous among all particles. Further, from the viewpoint of high absorbing rate, the crosslinked polymer particles having a BET specific surface area of not less than 0.025 $m^2/g$, preferably not less than 0.03 $m^2/g$ and more preferably not less than 0.04 $m^2/g$ based on particles having a size ranging from 300 to 600 μm may be adopted. The manufacturing method of the present invention has an advantageous feature in that even when adopting irregular crushed shape water-absorbent resin, porous absorbent resin or fine recycled absorbent resin powders in which a crosslinking agent is likely to remain as a residue because of its high specific surface area, the water-absorbent agent powders without a residue of the crosslinking agent or with a small amount of a residue can be obtained.

In the present invention, in the case of using the foamed porous hydrophilic polymer as the resin precursor, although a method of boiling and then foaming the hydrogel polymer when carrying out a polymerization or drying may be used, it is preferable to use the foaming agent when manufacturing the resin precursor. Examples of the foaming agent to be used in the present invention may be but are not limited to:

an inactive gas such as nitrogen, various organic solvents such as methyl alcohol, cyclohexane, etc.;

carbonates such as sodium (hydrogen)carbonate, ammonium (hydrogen)carbonate, potassium (hydrogen) carbonate, magnesium carbonate, carbon dioxide, ethylene carbonate, etc.;

water-soluble azo compounds such as 2,2'-azobis(2-methylpropionamizine) dihydrochloride, 2,2'-azobis(2-(2-imidazoline-2-il)propane) dihydrochloride, 2,2'-azobis [2-methyl-N-(2-hydroxyethyl)-propionamide], etc.; and water uniformly dispersed azo compounds such as 2,2'-azobis(2-methylpropioneamizine)diacrylate, etc.

Among these foaming agent, a water soluble or water dispersable azo compound, or carbonate is preferable, and further from the view point of controlling foams, a water-soluble polymer or a surfactant may be used in combination.

Although a suitable amount of such foaming agent, water soluble polymer or surfactant varies, it is normally based on the total amount of the monomer component, not more than 200 percent by weight, preferably not more than 100 percent by weight in the case of carbonates; not more than 5 percent by weight in the case of the azo compound, preferably not more than 1 percent by weight; in the case of the water soluble polymer, not more than 10 percent by weight, and in the case of the surfactant not more than 2 percent by weight and more preferably not more than 1 percent by weight.

As to the particle size of the resin precursor, those having an average particle diameter ranging from 200 $\mu$m to 600 $\mu$m, and not more than 10 percent by weight of the resin including particles having a diameter of less than 150 $\mu$m are the most preferable. In the case of adopting the particles having an average diameter of less than 200 $\mu$m, a sufficient improvement in absorbency under pressure may be difficult to be achieved. On the other hand, when adopting particles having an average diameter of above 600 $\mu$m, the absorbing rate would be low, and thus, a long time would be required for reaching a saturated amount of absorption. On the other hand, when the resin having a particle diameter of less than 150 $\mu$m exceeds 10 percent by weight, an amount of a residue of the crosslinking agent is difficult to be reduced.

The resin precursor to be used in the present invention has water content ranging from 1 to below 50 percent, preferably ranging from 1 to below 20 percent and still more preferably less than 10 percent. It is yet still more preferable that such resin precursor is in the form of powder. If the water content is high, the crosslinking agent having an epoxy group is penetrated into the inside of the resin precursor, and a reduction in an amount of a residue of the crosslinking agent having an epoxy group can be expected. On the other hand, however, the absorbency is lowered, and improvement in water-absorbent properties under high pressure cannot be expected.

In the present invention, the resin precursor having a carboxyl group obtained in the described manner is heat-treated by adding a crosslinking agent having an epoxy group as an essential component and surface regions of the resin precursor are crosslinked to obtain the water-absorbent resin powders, in which a residue of the crosslinking agent having an epoxy group remains is used as a starting material.

In the case where the water-absorbent resin powders which are crosslinked by a crosslinking agent having an epoxy group do not contain the residue of the crosslinking agent, if such water-absorbent resin powders are used as a starting material, in general, the problem is raised in that the water-absorbent agent powders resulting from the water-absorbent resin powders do not show sufficient absorbency both without pressure and under high pressure probably because a uniforms crosslinkage only on the particle surface layer of the water-absorbent resin are not obtained. For the reason set forth above, it is not preferable to adopt such water-absorbent resin powders as a starting material. In the present invention, it is further preferable that the crosslinking agent having an epoxy group is added to the resin precursor in the form of an aqueous solution and then heated. Based on 100 parts by weight of the resin precursor prior to be crosslinked at its surface, the crosslinking agent having an epoxy group is used in an amount ranging from 0.005 to 2 parts by weight, preferably ranging from 0.02 to 1.5 parts by weight, and still more preferably ranging from 0.06 to 1 part by weight, while the aqueous solution including the crosslinking agent is used preferably in an amount ranging from 0.1 to 10 parts by weight.

Here, the aqueous solution is water or a mixture of water and hydrophilic organic solvent.

After adding the aqueous solution, the heating temperature preferably ranges from 50 to 230° C., and more preferably from 100 to 200° C. It is further preferable that the heat-treated absorbent resin powders contain a solid portion of above 90 percent, more preferably not less than 95 percent, and still more preferably not less than 98 percent.

When respective amounts of the crosslinking agent and the aqueous solution to be added deviate from the described range, improvement in water-absorbent properties such as absorbency under high pressure may not be obtained, or an amount of a residue of the crosslinking agent having an epoxy group may not be reduced even after carrying out the process.

The crosslinking agent having an epoxy group of the present invention is a compound reactive to a plurality of carboxyl groups in the resin precursor, which has at least one epoxy group in a molecule.

Such compound may be, but is not limited to:

glycidyl ethers such as ethylene glycol diglycidyl ether, polyethylene diglycidyl ether, glycerol polyglycidyl ether, diglycerol polyglycidyl ether, polyglycerol polyglycidyl ether, propylene glycol diglycidyl ether, polypropylene glycol diglycidyl ether, etc.;

glycidyl compounds such as glycidol, γ-glycidoxypropyltrimethoxysilane, etc.;

epihalohydrins such as epichlorohydrin, epibromohydrin, etc.;

phosphonic acid glycidyl ethers such as methyl phosphonic acid diglycidyl ether, n-propyl phosphonic acid diglycidyl ether, etc.;

cyclic epoxy compounds such as 3,4-epoxycyclohexane carboxylic acid-3',4'-epoxycyclohexyl ester (product name: Celoxide R 2021, DAICEL Chemical Industries LTD), and the like.

Among all, from the viewpoint of water-absorbent properties of the water-absorbent agent powders, the polyglycidyl compounds are preferable, and polyglycidyl ethers such as ethylene glycol diglycidyl ether is still more preferable as the crosslinking agent having an epoxy group.

In the present invention, the described crosslinking agent having an epoxy group may be used in combination with another crosslinking agent that is reactive with a carboxyl group. Such crosslinking agent may be the below-listed known crosslinking agents for use in crosslinking the surface regions of the compound. Examples of such surface crosslinking agent may be, but are not limited to:

polyhydroxy alcohol compounds such as ethylene glycol, diethylene glycol, propylene glycol, triethylene glycol, tetraethylene glycol, polyethylene glycol; propylene glycol, 1,3-propanediol, dipropylene glycol, 2,2,4-trimethyl-1,3-pentanediol, polypropylene glycol, glycerol, polyglycerol, 2-butene-1,4-diol, 1,4-butanediol, 1,5-pentanediol, 1,6-hexanediol, 1,2-cyclohexanedimethanol, 1,2-cyclohexanol, trimethylol propane, diethanolamine, triethanolamine, polyoxypropylene, oxyethylene-oxypropylene block copolymer, pentaerythritol, sorbitol, etc.;

polyamine compounds such as ethylenediamine, diethylenetriamine, triethylenetetramine, tetraethylene pentamine, pentaethylenehexamine, polyamidepolyamine, polyethyleneimine, etc., and condensation products of these polyamine compounds and haloepoxy compounds;

polyisocyanate compounds such as 2,4-tolylene diisocyanate, hexamethylene diisocyanate, etc.;

polyoxazoline compounds such as 1,2-ethylene bisoxazoline, etc.;

a silane coupling agent such as γ-glycidoxypropyltrimethoxysilane, γ-aminopropyltrimethoxy silane, etc.;

alkylene carbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, 1,3-dioxopane-2-one, etc.; and polyvalent metallic compounds such as hydroxides and chlorides of metals such as zinc, calcium, magnesium, aluminum, iron, zirconium, etc. Only one kind of the above-listed crosslinking agent may be adopted, or two or more kinds thereof may be suitably mixed and adopted.

The water-absorbent resin powders having a carboxyl group containing a residue of a crosslinking agent having an epoxy group, obtained by the described method are formed into water-absorbent agent powders of the present invention by reducing the amount of the residue by the method 1): adding a nucleophilic reagent to water-absorbent resin powders in a form of powder under an applied heat or the method 2): washing water-absorbent resin powders. By carrying out at least either one of the post processes 1) and 2), desirable water-absorbent agent powders of the present invention, that show desirable absorbing characteristics while reducing the amount of the residue of the crosslinking agent can be achieved efficiently at low cost.

First, the first method of manufacturing water-absorbent agent powders characterized in that an amount of the residue of the crosslinking agent is reduced by adding a nucleophilic reagent to heated water-absorbent resin powders having a carboxyl group, in which surface regions are crosslinked by a crosslinking agent having an epoxy group, and a residue of the crosslinking agent is contained, will be explained in detail.

In the present invention, it is an essential condition that the water-absorbent resin powders to be processed are heated. In the case of adopting the water-absorbent resin powders at room temperature or cooled off at below room temperature without heat, it is extremely difficult to supply the water-absorbent resin powders stably and continuously, and thus it is difficult to industrially manufacture the water-absorbent agent powders in practical applications or to ensure quality water-absorbent agent powders. Sufficient effects of reducing the amount of a residue of the crosslinking agent cannot be expected also because the absorbing rate or adsorbing rate of the nucleophilic reagent into the water-absorbent resin powders is too low. Such problems are not very obvious when manufacturing the water-absorbent powders in a small amount, i.e., for example, in an experimental level. However, with an increase in production of the water-absorbent agent powders to the industrial production level, the inventors of the present invention have faced the described problems, and have coped with the problems to find the solution. Inventors of the present invention have succeeded in solving such problems in a simple and efficient manner, i.e., by heating beforehand the water-absorbent resin powders to be processed.

To be specific, it is an essential condition that the heating temperature of the water-absorbent resin powders is above room temperature. Further, in order to solve the described problems, the heating temperature is required to be not less than 30° C., preferably not less than 35° C., and more preferably not less than 40° C.

The water-absorbent resin powders can be supplied stably and continuously by setting the heating temperature to above room temperature, preferably not less than 30° C., and more preferably not less than 35° C. It should be noted here that if the temperature of the water-absorbent resin powders is too high, the absorbing rate or the adsorbing rate of the nucleophilic reagent into the water-absorbent resin powders becomes too high, which generates a non-uniform mixture, or an amount of the residue of the crosslinking agent may be reduced in a smaller amount.

In consideration of the above, the upper limit of the temperature of the water-absorbent resin powders is normally at below 200° C., preferably at below 100° C., and more preferably at below 80° C. The upper limit temperature below 65° C. is still more preferable.

The water-absorbent resin powders are heated beforehand, i.e., an essential condition of the present invention, by externally applying heat to the water-absorbent resin powders to a predetermined temperature before the nucleophilic reagent is added, for example, by a dielectric heater, a contact-type heater, a hot air heater, etc. It is also permitted to adjust the heating temperature to a predetermined temperature or the temperature at which the water-absorbent resin powders is kept after being heated, i.e., after being polymerized, dried, pulverized, surface-crosslinked, etc.

In the present invention, a nucleophilic reagent is added to the heated water-absorbent resin powders having a carboxyl group, which contain the residue of the crosslinking agent having an epoxy group.

In the present invention, the powder form suggests a state where the water-absorbent resin powders do not form a block by contacting each other and can be ground with ease even after the nucleophilic reagent is added without being formed into a gel by swelling, and the powdered state thereof is maintained even after the treatment.

When processing with the nucleophilic reagent, in the case that the water-absorbent resin powders are not in a powdered form, the amount of the residue of the epoxy crosslinking agent cannot be reduced to a sufficient level, or the absorbing rate or absorbency under pressure may be lowered after the nucleophilic reagent treatment. Thus, the object of the present invention, i.e., to reduce the amount of the residue of the crosslinking agent, to improve the absorbency under high pressure and the absorbing rate may not be fully satisfied in the above case.

A suitable nucleophilic reagent for the present invention may be, but is not limited to: nucleophilic reagents having a nucleophilic atom of a carbon or oxygen, nitrogen compounds having a nucleophilic atom of nitrogen, halogen compounds having a nucleophilic atom of halogen, sulfur compounds having a nucleophilic atom of sulfur, phosphorous compounds having a nucleophilic atom of phosphorous, a nucleophilic reagent having a nucleophilic point of a hydrogen group, a nucleophilic reagent having a nucleophilic point of a carboxyl group, etc.

The nucleophilic reagent having a nucleophilic atom of carbon or oxygen may be acetals, acetoacetates, alcoholates, acetonitriles, acetylenes, acid anhydrides, water, alcohols, inorganic hydroxides, aldehydes, organic peroxides such as organic hydroperoxides, hydroxymethyl urea, carbon dioxide, carboxylic acids, cyanoacetates, olefins such as cyclopentadiene, ketones, malonic acids, phenols, etc.

Nitrogen compounds having a nucleophilic atom of nitrogen may be, but are not limited to: nitrates of alkaline-earth such as barium nitrate, amides, primary amine compounds, secondary amine compounds, tertiary amine compounds, polyamine compounds, ammonia, ammonium carbonate, azides, cyanamides, (iso)cyanates, ethyleneimine, hydrazine compounds, lactam compounds, futalimide, sulfonamides, pyridine, nicotine amide, urea, thiourea, etc.

Halogen compounds having a nucleophilic atom of halogen may be acyl halides such as acetyl chloride, etc., alkyl halides, antimony trihalogen, bismuth halide, boron halides such as boron trioxide, etc., carbamoyl halides such as carbamoyl chloride, etc., chlorosilane compounds, etc.

Sulfur compounds having a nucleophilic atom of sulfur may be but are not limited to: aminothiols, carbon disulfide, ethylene sulfide, hydrogen sulfide, sulfurous acid (sulfite), hydrogen sulfurous acid (hydrogen sulfide), thiosulfate (thiosulfide), etc. Phosphorous compounds having a nucleophilic atom of phosphorous may be phosphate.

Among the nucleophilic reagents having a nucleophilic atom of oxygen, those, in which a nucleophilic point can be a hydrogen group, may be but are not limited to: water, propylene glycol, sodium hydroxide, potassium hydroxide, polyethylene glycol, butyl alcohol, alkoxy(poly)ethylene glycol, etc. Examples of the nucleophilic reagent in which the carboxyl group may be a nucleophilic point may be, but are not limited to lactate, citrate, propionate, etc.

In the present invention, it is preferable to adopt the neutral or basic nucleophilic reagent having a pH of not less than 5. The nucleophilic reagent may be solid, liquid or gas at room temperature. In order to achieve the object of the present invention, the nucleophilic reagent that is liquid at room temperature is preferable. Further, in view of properties, as a large amount of the residue of the nucleophilic reagent may damage the absorbency, volatile liquid that can be removed with ease after the treatment is preferable. It is also preferable that the nucleophilic reagent has a boiling point of not less than 60° C., more preferably not less than 100° C. On the other hand, it is preferable that the upper limit of the boiling point of the nucleophilic reagent is not more than 150° C. It is further preferable that the nucleophilic reagent includes water as an essential component in view of not only reducing the amount of a residue of a crosslinking agent but also improving the absorbing rate.

For example, in the case where liquid such as water is used for the nucleophilic reagent, the amount of use of the liquid is normally in a range of from 1 to 30 percent by weight with respect to water-absorbent resin powders, preferably in a range of from 2 to 20 percent by weight, more preferably in a range of from 3 to 10 percent by weight, and still more preferably in a range of from 4 to 8 percent by weight. In the case where the amount of use of water is above the range, sufficient effects of reducing the amount of a residue of a crosslinking agent for the amount of use cannot be obtained. Moreover, the absorbency under load or the absorbing rate may be lowered. Additionally, when adding water with respect to the water-absorbent resin powders, water may be added in a form of mist, moisture, steam, etc.

In the present invention, a liquid nucleophilic reagent, preferably volatile liquid, more preferably water, and at least one kind of a nucleophilic reagent in which a nitrogen and/or sulfur atom may be a nucleophilic point is used in combination with the liquid nucleophilic reagent from the view of absorbing characteristics such as reducing the amount of a residue of a crosslinking agent having an epoxy group, improving the absorbing rate of the water-absorbent agent powders, etc.

The nucleophilic reagent is absorbed by the water-absorbent resin powders, and preferably, it is absorbed or adsorbed by the water-absorbent resin powders from the surface of reducing an amount of a residue of the crosslinking agent. When adding the nucleophilic reagent, it is further preferable that at least one member selected from the group consisting of water-soluble surface active agent and the water-soluble polymer be added simultaneously or separately in order to prevent a reduction in absorbing rate by the surface crosslinkage in the absorbent resin powders, and thus the polymer shows a still improved absorbing rate.

Further, for the nucleophilic reagent to be used together with water, from the view of safety and effect, amines, ammonia, ammonium carbonate, sulfurous acid (sulfite), hydrogen sulfurous acid (hydrogen sulfide), thiosulfate (thiosulfide), urine, thiourine, etc., is preferable, and polyamine and/or hydrogen sulfurous acid (hydrogen sulfide) is the most preferable.

Such compound may be, but is not limited to sodium bisulfite, potassium bisulfite, ammonium bisulfite, polyallyl amine, poly(diallyl amine), poly(N-alkyl allyl amine), poly (alkyldiallyl amine), a copolymer of monoallyl amine and diallyl amine, a copolymer of monoallyl amine and N-alkylallyl amine, a copolymer of monoallyl amine and dialkyl diallyl ammonium salt, a copolymer of diallyl amine and dialkyl diallyl ammonium salt, straight chain polyethylene imine, branched chain polyethylene imine, polyethylene polyamine, polypropylene polyamine, polyamide polyamine, polyether polyamine, polyvinyl amine, polyamide polyamine-epichlorohydrine resin, etc.

In the present invention, the amount of use of the nucleophilic reagent of the volatile liquid which is preferably used in combination with water differs depending on the amount of residual nucleophilic reagent including an epoxy group for use in crosslinking the surface of the water-absorbent resin. However, it is normally in a range of from 0.005 to 10 parts by weight, preferably in a range of from 0.01 to 5 parts by weight, and still more preferably in a range of from 0.1 to 3 parts based on 100 parts by weight of a solid portion of the water-absorbent resin powders.

It is not preferable to use the nucleophilic in an amount of more than 10 parts by weight in an economical aspect. Moreover, this causes an excess amount in achieving the desirable effects of reducing the amount of a residue of a crosslinking agent, or it may cause the absorbency under pressure to be lowered. On the other hand, if the nucleophilic reagent is used in an amount less than 0.005 parts by weight, a sufficient improvement in absorbency under high pressure or absorbing rate may not be ensured, thereby presenting the problem that the desirable effects of reducing the amount of a residue of the crosslinking agent cannot be obtained. In consideration of the above, it is more preferable that the amount of use of the above nucleophilic reagent is in a range of from 0.02 to 2 parts by weight.

In the present invention, in the case of adopting water as the nucleophilic reagent, other than water, hydrophilic organic solvent may be used in combination. A presence or absence of nucleophilicity of the hydrophilic organic solvent does not matter.

Such hydrophilic organic solvent may be, but is not limited to:

lower alcohols, such as methyl alcohol, ethyl alcohol, n-propyl alcohol, isopropyl alcohol, n-butyl alcohol, isobutyl alcohol, and t-butyl alcohol;

ketones, such as acetone;

ethers, such as dioxane, alkoxy(poly)ethylene glycol, tetrahydrofuran, etc.,;

amides, such as N,N-dimethylformamide, etc.; and sulfoxides, such as dimethylsulfoxide, etc.

An amount of use of the hydrophilic organic solvent varies depending on the kind and particle size of the water-absorbent resin powders; however, a preferred range with respect to 100 parts by weight of the solid content of the water-absorbent resin powders is normally in a range of from 0 to 10 parts by weight, preferably less than 5 parts by weight.

In the present invention, water-absorbent resin powders having a carboxyl group, in which a residue of a crosslinking agent having an epoxy group remains can be formed into water-absorbent agent powders of the present invention which have a significantly reduced amount of a residue of the crosslinking agent by adding the described nucleophilic reagent and, desirably, have an improved absorbing rate.

Further, processes of the present invention are preferably carried out in such a manner that a reaction between the residue of the crosslinking agent having an epoxy group with a nucleophilic reagent does not affect the absorbing characteristics of the water-absorbent agent powders. The method of carrying out such processes is not particularly limited as long as the powdered nucleophilic reagent can be uniformly added to the water-absorbent resin, and, for example, the following method may be adopted:

1) The water-absorbent resin powders are reacted with the nucleophilic reagent on contact therewith in a form of gas;
2) The nucleophilic reagent is mixed with the water-absorbent resin powders to be reacted therewith;
3) A solution containing the nucleophilic reagent is mixed with the water-absorbent resin powders to be reacted therewith; or
4) Water-absorbent resin powders are brought into contact with the solution containing the nucleophilic reagent to be reacted therewith, etc.

It is further preferable that the reaction is completed in a short period of time so that the absorbing characteristics of the water-absorbent agent powders are not adversely affected by applying an auxiliary treatment such as heating, or adding a catalyst, etc., if necessary.

When processing the water-absorbent resin powders with the nucleophilic reagent, the following devices are preferably adopted: a fluidized bed mixer, a cylindrical mixer, a screw mixer, a turbulizer, Nauta mixer, a V-shaped mixer, a ribbon type mixer, a twin arm type kneader, an airborne mixer, a rotary disk mixer, a roll mixer, an airborne dryer, a shelf-type rotary dryer, a paddle dryer, a rotary disk dryer, a fluidized bed dryer, a belt-type dryer, paddle dryer, a rotary disk dryer, a belt-type dryer, a Nauta heater, an infra red ray dryer, a microwave dryer, etc.

In order to achieve the above object, it is preferable to apply a heat treatment in a presence of a nucleophilic reagent, and more preferably to dry it after the heat treatment. Heating time and temperature are determined appropriately in consideration of the kind and amount of the nucleophilic reagent, and an amount of reduction of the residue of the crosslinking agent. However, sufficient effects cannot be achieved if an application time is too short. In the case of adopting water, a heat treatment is preferably applied for more than 5 minutes, normally, from 6 to 1,000 minutes, preferably from 10 minutes to 600 minutes, and more preferably from 20 to 300 minutes.

In the present invention, it is preferable to apply a heat treatment to water-absorbent resin powders by setting the temperature of the material for the water-absorbent resin powders so that at least a part of a liquid nucleophilic agent contact with the water-absorbent resin powders in a vapor state steam. Here, the temperature of the material for the water-absorbent resin powders is set to not more than 150° C., more preferably not more than 100° C. Further, in the case where a drying treatment is applied simultaneously with a heat application process, or separately from the heat application process, the content of the final water-absorbent resin powders is not less than 90 percent by weight to the water-absorbent agent powders, and more preferably not less than 95 percent by weight, to ensure desirable characteristics.

In the first method (process with the nucleophilic reagent) of the present invention, in the case of adopting water for the nucleophilic reagent, it is preferable to apply a heat treatment to a mixture resulting from adding water to the water-absorbent resin powders having a carboxyl group in a powdered form. Surface regions of the water-absorbent resin powders are crosslinked by a crosslinking agent having an epoxy group and include a residue of the crosslinking agent. The water-absorbent resin powders manifest improved absorbency under pressure of at least 20 g/g with respect to a physiologic saline solution under load of 50 g/cm² by the crosslinkage, a part of the particles thereof being foamed.

Other than the above, an amount of a residue of the crosslinking agent can be reduced by leaving the water-absorbent resin powders at room temperature for not less than 10 days. In this case, sufficient effects of reducing the amount of a residue of the crosslinking agent cannot be expected in a short period of time, and it is required to leave the water-absorbent resin powders having water absorbed therein or added thereto, for not less than ten days, preferably not less than 20 days, more preferably not less than 30 days. Here, the desirable amount of water to be added is as described earlier, and it may be preferable to add such water partially as moisture, etc., continuously.

In the present invention, if a large amount of the nucleophilic reagent is added all at the same time, the problem may be raised in that the absorbency under pressure is reduced. Thus, in order to reduce the amount of a residue of the crosslinking agent effectively, it is preferable to divide the nucleophilic reagent to be repetitively added little by little.

In the present invention, it is preferable that in the water-absorbent agent powders processed with the nucleophilic reagent, the amount of the crosslinking agent having an epoxy group is reduced to not more than 2 ppm, more preferably to not more than a lower detectable limit (hereinafter referred to as ND). It is further preferable that the absorbency under pressure of the water-absorbent agent powders is kept at not less than 20 g/g, more preferably at not less than 25 g/g, while manifesting high absorbing rate. The described three beneficial properties can be accomplished by the method of the present invention.

Next, the second method will be explained which is characterized in that surface regions of the water-absorbent resin powders are crosslinked by the crosslinking agent having an epoxy group, and an amount of a residue of the crosslinking agent is reduced by washing the water-absorbent resin powders having a carboxyl group, in which a residue of the crosslinking agent having the epoxy group remains.

The washing treatment suggests the process of making (i) the water-absorbent resin powders having a carboxyl group in which the crosslinking agent having an epoxy group remains, in contact with a washing agent in gas, solid, or liquid that can remove the crosslinking agent, and (ii) subsequently separating the washing agent from the water-absorbent resin powders.

In this case, a washing treatment is carried out by a method of separating a mixed solution from the water-absorbent resin powders preferably after contacting the water-absorbent resin in contact with the liquid, more preferably after contacting it with an organic solvent, more preferably by a method of separating the mixed solution from water-absorbent resin powders after contacting the powders with a mixed solution composed of water and hydrophilic organic solvent.

For the organic solvent, those of a low boiling point, i.e., less than 150° C., preferably less than 100° C. are preferable. Although it is permitted to use a hydrophobic organic solvent such as cyclohexane, etc., the hydrophilic organic solvent is preferable in terms of efficiency such a as lower ketone such as acetone; etc. For the hydrophilic solvent to be mixed with water, lower alcohol, etc., such as methyl alcohol, ethyl alcohol, propyl alcohol, isopropyl alcohol, t-butyl alcohol, etc., is preferable.

It is further preferable that the mixed ratio of water and hydrophilic organic solvent is selected such that the water-absorbent resin powders are not swollen with the mixed solution. In this case, the mixed ratio differs depending on a chemical composition of the water-absorbent resin powders. However, the percent by weight of the mixed ratio can be confirmed by a preliminary test with ease.

In most cases, the ratio (percent by weight) of water and hydrophilic organic solvent is water: hydrophilic organic solvent=1~50: 99~50. The amount of use of the washing solution is determined based on the amount of a residue of a crosslinking agent in the water-absorbent resin powders and the washing solution. It is typically used in an amount of from 50 to 2,000 parts by weight, more preferably from 100 to 1,000 parts by weight to 100 parts by weight of the water-absorbent resin powder.

In the present invention, when making the mixed solution of water and hydrophilic organic solvent, the contact is carried out by the continuous or non-continuous batch process.

For example, when adopting the method in which the water-absorbent resin agent powders are made in a mixed solution composed of water and hydrophilic organic solvent, the water-absorbent agent powders are made by following process: the water-absorbent resin powders are contacted with the mixed solution due to stirring if necessary, and subsequently, the water-absorbent resin powders are washed by separating them from the mixed solution by decantation or suction by filtering. In the case of continuously carrying out a washing treatment, the flow of the water-absorbent resin powders and the washing solution can be in both the same direction and the countercurrent direction. However, in terms of washing effect, the countercurrent direction is preferable. In the batch system, the number of times a washing treatment is carried out by batch process is not particularly limited.

In each of the described methods, a washing treatment is typically carried out in a range of from 15 seconds to 2 hours, preferably from 30 seconds to 60 minutes, and more preferably from 1 minute to 30 minutes. A wide range is applicable for the temperature of the liquid and powders when washing. However, it is preferable that the washing temperature is above room temperature, more preferable from 30 to 100° C., more preferably from 40 to 80° C., and still more preferably from 40 to 60° C. The described washing treatment may be carried out under an applied pressure, reduced pressure or normal pressure. However, it is typically carried out under normal pressure. The water-absorbent resin powders after carrying out the washing treatment may be dried, if necessary. In the water-absorbent agent powders, the amount of a residue of the cross-linking agent having an epoxy group is preferably not more than 2 ppm, more preferably not more than ND. It is further preferable that the absorbency under pressure of the water-absorbent agent powders is not less than 20 g/g, more preferably not less than 25 g/g. These properties are achieved by the method of the present invention.

In the described first method (treatment with a nucleophilic reagent) and the second method (washing treatment), in order to prevent a drop in absorbing rate by the surface crosslinkage and improve the absorbing rate, at least one of the water-soluble polymer and the surfactant, preferably, the water-soluble surfactant is used together with the nucleophilic reagent and the washing agent. To be specific, such material may be added separately from the nucleophilic reagent and the washing agent, more preferably with the water-soluble surfactant with the nucleophilic reagent and the washing agent. Here, it is more preferable that water be added when adding these additives.

The present invention provides a method of manufacturing water-absorbent agent powders made from water-absorbent resin powders, which are surface crosslinked and dried water-absorbent resin powders to which at least one member selected from the group consisting of the water-soluble surfactant and the water-soluble polymer are added in a sufficient amount to increase the absorbing rate of water-absorbent resin powders, the absorbing rate being defined as 28 times swelling time with an artificial urine.

The above water-absorbent resin powder has an irregular crushed shape whose absorbency under load of 50 g/cm$^2$ is increased to at least 20 g/g based on the physiologic saline solution by the surface crosslinkage. It is preferable that the water-absorbing rate be heightened by not less than 0.02 (g/g/sec), more preferably before adding, more preferably by not less than 0.05 (g/g/sec), and more preferably by not less than 0.1 (g/g/sec) compared with the water-absorbing rate before adding the above material.

As described, it has been found that when carrying out a surface crosslinkage with a crosslinking agent having an epoxy group, in order to increase the absorbency under high pressure that is durable under a heavy weight, specifically, when the absorbency under pressure with respect to the physiologic saline solution under an applied load of 50 g/cm$^2$ is increased to not less than 20 g/g, the absorbing rate (g/g/sec) based on 28 times swelling time with artificial urine may be dropped on the contrary.

However, like the present invention, it is preferable to add the water-soluble surfactant or the water-soluble polymer, and is more preferable to further add water since the water-absorbent agent powders in which a drop in absorbing rate by the surface crosslinking is suppressed can be obtained while maintaining the absorbency under high pressure compared with the state where the process of the present invention has not been applied. For the crosslinking agent to be adopted for the surface crosslinkage, the crosslinking agent having an epoxy group as the surface crosslinking agent is especially preferable. However, other crosslinking agents may be used.

For the surfactant to be adopted in the present invention, a nonionic or anionic surfactant, preferably nonionic surfactant having HLB (Hydrophile-Lipophile Balance) of not less than 7, more preferably not less than 9, and still more preferably not less than 11 may be used.

The amount of use of the surfactant is preferably in a range of from 0.001 to 2 parts by weight, more preferably in a range of from 0.01 to 1 part by weight, more preferably in a range of from 0.02 to 0.5 parts by weight based on 100 parts by weight of water-absorbent resin powders. If the surfactant is used in an amount less than 0.01 parts by weight, a sufficient adding effect cannot be obtained. On the other hand, when the surfactant is added in an amount greater than 2 parts by weight, a sufficient effect of improving the absorbing rate for the amount of surfactant to be added cannot be obtained. Moreover, the absorbency under pressure may be dropped on the contrary, i.e., undesirably reduced.

Examples of the water-soluble polymer may be but are not limited to: a water soluble polymer such as starch, methylcellulose, carboxymethylcellulose, hydroxyethylcellulose, polyalkyleneoxide, polyacrylic acid, polyacrylate salt, etc. It is preferable that water-soluble polymer be a nonionic or anionic water-soluble polymer.

Examples of the anionic surfactant to be used in the described surfactant may be but are not limited to: sodium oleate, fatty acid salt such as potassium castor oil, sodium laurylsulfate, alkylsulfate such as ammonium lauryl sulate, etc., alkyl benzene sulfonate such as sodiumdodecylbenzene sulfonate, etc., alkyl naphthalene sulfonate, dialkyl sulfosuccinate, alkyl phosphate, naphtalenesulfonic acid formalin condensate, polyoxyethylene alkyl sulfate, etc.

Examples of the nonionic surfactant to be used in the described surfactant may be but are not limited to: polyoxyethylenealkylether, polyoxyethylenealkylphenol ether, polyoxyethylene fatty acid ester, polyoxyethylene sorbitan fatty acid ester, polyoxy ethylenealkylamine, fatty acid ester, oxyethylene-oxypropylene block polymer, etc.

Examples of the cationic surfactant to be adopted in the surfactant may be but are not limited to: alkyl amine salt such as lauryl amine acetate, stearylamine acetate, etc., quatenary ammonium salt such as lauryl trimethylammonium chloride, stearyltrimethylammonium chloride, etc.

For the amphoteric surfactant to be adopted as the described surfactant, lauryl dimethylamineoxide, etc., may be used.

As described, with regard to the first method and the second method, in order to achieve the object of the present invention, the present invention provides a method of manufacturing water-absorbent resin powders being dried having a carboxyl group, in which to water-absorbent resin powders of irregular crushed type in which the surface thereof is crosslinked, having an absorbency under pressure with respect to a physiologic saline solution under load of 50 g/cm$^2$ is increased to at least 20 g/g, at least one member selected from the group consisting of a water-soluble surfactant and a water-soluble polymer is added in a sufficient amount exceeding an absorbing rate of the water-absorbent resin powders after the surface crosslinking treatment, the absorbing rate being defined by 28 times swelling time with artificial urine.

The manufacturing method of the water-absorbent agent powders of the present invention enables new water-absorbent agent powders to be manufactured. To be specific, the present invention provides well-balanced properties which are mutually contradictory and cannot be obtained by the conventional methods, i.e., absorbency under pressure, absorbing rate, an amount of a residue of the epoxy crosslinking agent.

The water-absorbent agent powders resulting from the present invention are at least partially porous and exhibit a reduced amount of a residue of the crosslinking agent of from 1/several tens to 1/several hundreds times of that of the convention water-absorbent agent powders in spite of a large surface area.

Namely, the water-absorbent agent powders of the present invention are at least partially porous and surface regions are crosslinked by a crosslinking agent having an epoxy group, and an amount of a residue of the crosslinking agent is reduced to not more than 2 ppm, and more particularly to ND.

It is preferable that the water-absorbent agent powders exhibit an absorbency under load of 50 g/cm$^2$ based on a physiologic saline solution of not less than 20 g/m$^2$, more particularly not less than 25 g/m$^2$, while exhibiting an absorbency without pressure of not less than 35 g/g.

The water-absorbent agent powders have a BET specific surface area of resin powders (resin precursor) of not less than 0.025 m$^2$/g based on the resin powders having a particle diameter size ranging from 300 to 600 μm, more preferably not less than 0.03 m$^2$/g, more preferably not less than 0.04 m$^2$/g, and an absorbing rate defined herein of not less than 0.4 (g/g/sec) and preferably not less than 0.7 (g/g/sec).

The manufacturing method of the present invention enables water-absorbent agent powders to be manufactured efficiently, which exhibit excellent water-absorbent agent properties such as significantly reduced amount of a residue of a crosslinking agent by the nucleophilic reagent treatment while ensuring a sufficient absorbency under high pressure safely, befitting sanitary materials.

In the present invention, it is permitted for functions to add additives to the water-absorbent agent powders resulting from the present invention, such as a deodorizer, perfume, inorganic powders, foaming agent, pigment, dye, hydrophilic short fiber, plasticizer, binder, surface active agent, fertilizer, etc.

Such compounds are disclosed, for example, in U.S. Pat. Nos. 4,179,367, 4,190,563, 4,500,670, 4,693,713, 4,812, 486, 4,863,989, 4,929,717, 4,959,060, 4,972,019, 5,078,992, 5,229,488, EP Patent No. 0009977, EP Patent No. 0493011, etc.

It is further permitted to further granulate or mold the water-absorbent agent powders of the present invention. The granulating method is, for example, disclosed in U.S. Pat. No. 4,734,478, EP Patent No. 0450922, EP Patent No. 480031, etc.

PREFERRED EMBODIMENTS OF THE PRESENT INVENTION

In order that the invention may be more readily understood, the following non-limiting examples and comparative examples are given.

The present invention will be described in detail by way of examples and comparative examples. However, the present invention is not limited to the disclosure below.

The following method of various properties of the water-absorbent agent powders is measured by the following method.

(a) Absorbency Without Pressure

A sample, 0.2 grams of the water-absorbent agent powders was uniformly placed into a tea-bag like pouch (40 mm×150 mm) made of nonwoven fabric, immersed in an aqueous 0.9 percent physiological saline solution for 60 minutes. After leaving it for 60 minutes, the bag was taken out. The pouch was subjected to hydro-extraction for a predetermined period of time, and then weighed ($w_1$), while the tea bag-like pouch empty of the sample as a blank was processed in the same manner and then weighed ($W_0$). The absorbency without pressure (g/g) was calculated from the weights $W_1$ and $W_0$ in accordance with the following equation:

Absorbency without pressure (g/g)=(Weight $W_1(g)$-Weight $W_0$ (g))/Weight of Water-Absorbent Agent Powders 0.2 (g).

(b) Absorbency Under High Pressure

The measuring device to be used in measuring the absorbency under pressure will be explained in reference to FIG. 1.

Figure 1:
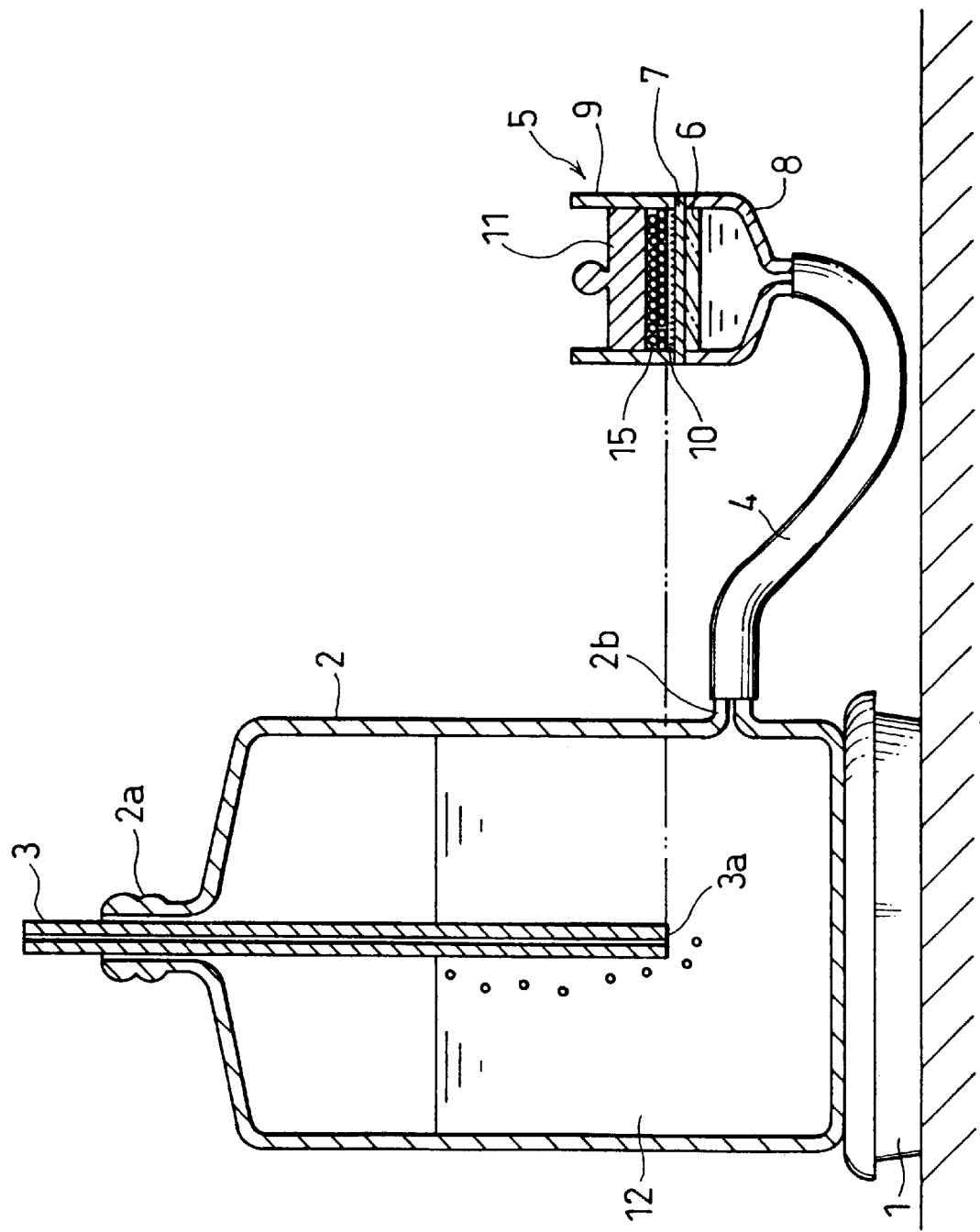
FIG. 1 is a device for measuring absorbency under high pressure to be used in the present invention.

As shown in FIG. 1, the measuring device includes a balance 1, a container 2 of a predetermined capacity placed on the balance 1, an air-intake pipe 3, a conduit 4, a glass filter 6, and a measuring section 5 placed on the glass filter 6.

The container 2 has an opening 2a on the top and an opening 2b on the side, and the air-intake pipe 3 is inserted through the opening 2a while the conduit 4 is fixed to the opening 2b. Further, a predetermined amount of the physiological saline solution 12 is poured in the container 2.

The lower end portion of the air-intake pipe 3 is dipped into the physiological saline solution 12. The air-intake pipe 3 is provided for keeping the pressure within the container 2 substantially at atmospheric pressure. The glass filter 6 has a diameter of, for example, 55 mm, and is mounted to a filter section 8 so as to close the upper end of the opening of the filter section 8.

The opening 2b on the side and the lower end opening of the filter section 8 is connected through the conduit 4 so that the inside of the container 2 and the inside of the filter section 8 communicate with each other through the conduit 4. The relative position and the height of the glass filter 6 to the container 2 are fixed. The measuring section 5 includes a paper filter 7, a supporting cylinder 9, a metal gauze 10 affixed to the bottom of the supporting cylinder 9, and a cylindrical weight 11.

The supporting cylinder 9 has the same inner diameter as the upper end opening of the filter section 8. The weight 11 is provided so as to be freely slidable in the axial direction of the supporting cylinder 9.

In the measuring section 5, the paper filter 7, and the supporting cylinder 9 (that is, the metal gauze 10) are sequentially placed on the glass filter 6 in this order, and the weight 11 is placed on the metal gauze 10 inside the supporting cylinder 9.

The metal gauze 10 is made of stainless steel to have a 400-mesh (the size of each mesh: 38 μm). The height position of the upper surface of the metal gauze 10, i.e., a contact surface between the upper surface of the metal gauze 10 and the water-absorbent agent powders 15 is set equivalent to the height of the lower end surface 3a of the air-intake pipe 3.

A predetermined amount of the water-absorbent agent powders is uniformly scattered on the metal gauze 10. The weight 11 is adjusted in such a manner to apply a load of 50 g/cm² evenly to the metal gauze 10, that is, the water-absorbent agent powders 15.

The absorbency under pressure of the water-absorbent agent powders was measured by using the above-arranged measuring device in the manner described below.

To begin with, preparatory operations are carried out, that is, a predetermined amount of physiological saline solution 12 was poured into the container 2, and the air-intake pipe 3 was inserted into the container 2. Then, the paper filter 7 was placed onto the glass filter 6. In the meantime, 0.9 g of water-absorbent agent powders were uniformly scattered inside the supporting cylinder, i.e., on the metal gauze 10, and the weight 11 was placed on the water-absorbent agent powders 15.

The metal gauze 10, that is, the supporting cylinder 9 having the water-absorbent agent powders and the weight 11 inside, is placed on the glass filter 6 in such a manner that the supporting cylinder 9 is coaxial to the glass filter 6.

Then, the weight of the physiological saline solution 12, which has been absorbed by the water-absorbent agent powders for 60 minutes since the supporting cylinder 9 was placed on the paper filter 7 was measured by the balance 1.

Then, in the same procedures but without the water-absorbent agent powders 15, the weight of the physiological saline solution 12 that was absorbed by the paper filter 7, etc., was calculated using the balance 1 as a blank value.

The absorbency (g/g) under high pressure with respect to the water-absorbent agent powders 15 was obtained by deducting the blank value, and the weight of the physiological saline solution 12 that is actually absorbed by the water-absorbent agent powders 15 divided by the initial weight (0.9 g) of the water-absorbent agent powders.

(c) Residual Amount of Crosslinking Agent Having an Epoxy Group in the Water-absorbent Resin Powders or the Water-absorbent Agent Powders A sample, 2.0 g of the water-absorbent agent powders was added to 100 ml beaker, and 2 ml of composite solution with a ratio of methyl alcohol/water of 2/1 percent by weight was added to the beaker, and then the beaker was closed with a tap, and was left for one hour. Then, 5 ml of methyl alcohol was added to the beaker and the content in the beaker was filtered off, and 1.0 g of the filtered solution was placed in an eggplant type flask, and 0.05 ml of 12 wt % of nicotine amide solution was added to the flask.

The air cooling tube was mounted to the eggplant type flask, and was heated for 30 minutes in a boiled water bath, and then the reactant solution in the flask was filtered by the paper filter. Next, after the filtered solution was concentrated, the additive of nicotine amide—crosslinking agent in the concentrated solution was analyzed by UV absorption using a high performance liquid chromatography.

On the other hand, in place of the water-absorbent agent powders, a predetermined amount of the crosslinking agent was added, and the line of the detected amount was determined to be an external standard, and an amount of a residue of the surface crosslinking agent (ppm) in the water-absorbent agent powders were calculated in consideration of the dilution rate of the filtered solution.

(d) Absorbing Rate (Swell Rate)

0.358 g of water-absorbent agent powders (having a particle size ranging from 300 to 850 μm) were dispersed in a glass test tube (with height of 126 mm) with an inner diameter of around 14.1 mm. Next, 10.0 g of artificial urine set to 25° C. was poured still at once from the top center. After 0.358 g of absorbent powders absorbed all of the urine by sight, a time required for forming a 28 times swollen gel (g/g) was measured in seconds, and the absorbing rate (g/g/sec) was obtained by dividing 28 times (g/g) with seconds. The larger the value of the absorbing rate becomes, the faster the water-absorbent agent powders absorb the urine. The artificial urine used in the present invention is a solution in which 0.2 percent by weight of sodium sulfate, 0.2 percent by weight of potassium chloride, 0.05 percent by weight of magnesium chloride hexahydrate, 0.025 percent by weight of calcium chloride dixahydrate, 0.085 percent by weight of ammonium dihydrogenphosphate, and 0.015 percent by weight of diammonium hydrogenphosphate were dissolved in water.

(e) Specific Surface Area

The area/weight ratio was obtained in the following manner. The powdered resin precursor classified into from 300 to 600 μm by a gauze of JIS standard was deaerated at 150° C. for 40 minutes, and the specific surface area was measured by the BET (Brunauer-Emmett-Teller) absorption method based on krypton gas while cooling with liquid nitrogen.

(f) Water-Soluble Component

After 0.5 g of water-absorbent resin powders are stirred for 16 hours with 1 liter deionized water, the swollen gel was removed with the paper filter. Then, the amount of polyanion obtained from the water-soluble polymer in the filtered solution was measured by the titrimetric colloid determination. By the measuring method, the water-soluble polymer, i.e., extractables eluted from the water-absorbent resin powders was measured in the water-absorbent resin powders.

(g) Solid Portion 1.000 g of water-absorbent resin powders were placed in an aluminum cup, and was dried at 180° C. for 3 hours in an oven with no wind. Then, the solid portion was measured based on its loss in weight on drying.

REFERENCE EXAMPLE 1

In 5,500 g (with monomer density of 37 percent) monomer solution of 75 mole percent neutralized acrylic acid sodium salt, 1.77 g (0.05 mole percent) of N,N'-methylene-bis acrylamide (inner crosslinking agent) was dissolved to obtain a mixed solution. After the mixed solution was deaerated for 30 minutes with nitrogen gas, it was supplied into a reactor of a covered kneader having an inner volume of 10 liters and equipped with two sigma vanes. The kneader is twin arm type equipped with a jacket and is made from stainless steel. While maintaining the mixed solution at 30° C., it was further replaced with nitrogen.

Next, with respect to the mixed solution, 2.40 g of sodium persulfate and 0.12 g of L-ascorbic acid were added to the mixed solution while agitating the mixed solution by the vanes. Then, a polymerization was started in one minute. After an elapse of time of 16 minutes, the peak of the temperature in the mixed solution, i.e., the polymerization reaction, reached 83° C.

The hydrogel polymer resulting from the polymerization reaction was substantially transparent without foam, and was subdivided into a diameter of around 5 mm. Then, after carrying out a polymerization reaction with further stirring for 60 minutes, the hydrogel polymer was taken out. The resulting finely divided hydrogel polymer was placed on a metal gauze of 300 μm (50 mesh) and dried under hot air at 150° C. for 90 minutes. Then, the resulting dried polymer was pulverized by a roll mill and further classified by a metal gauze of 850 μm mesh to obtain a resin precursor (A). The resulting resin precursor (A) had an irregular shape, and an average particle diameter of 360 μm, the resin precursor (A) having a content of resin having a particle diameter of less than 150 μm of 5 percent by weight and a water content of 6 percent by weight.

Figure 2:
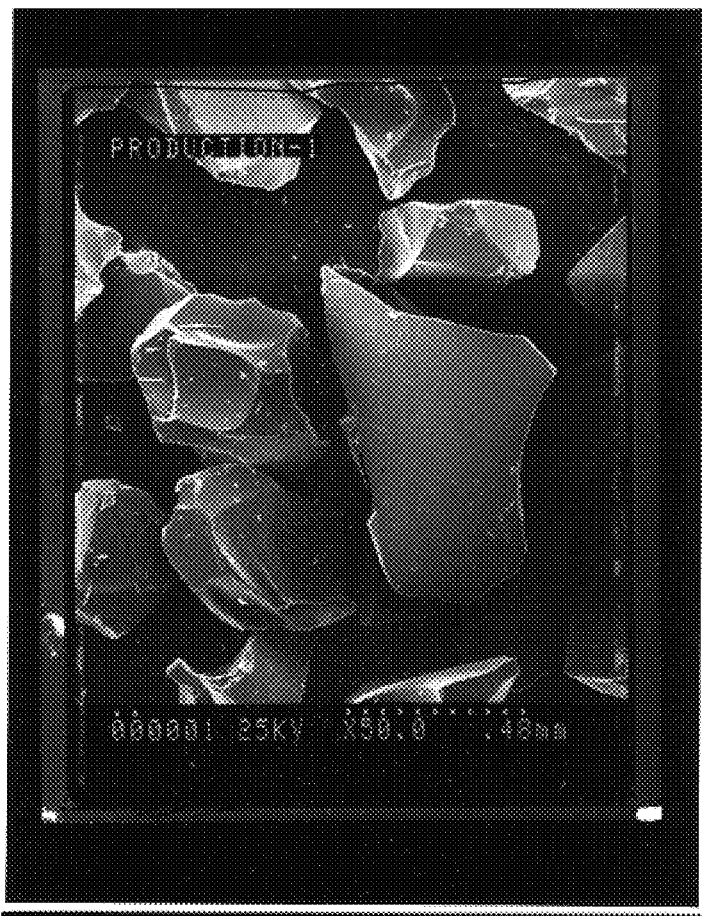
FIG. 2 is a 50 times enlarged electron micrograph of powders of the resin precursor (with a particle size ranging from 300 to 600 μm) in accordance with reference example 1 substituted for a drawing.
Figure 3:
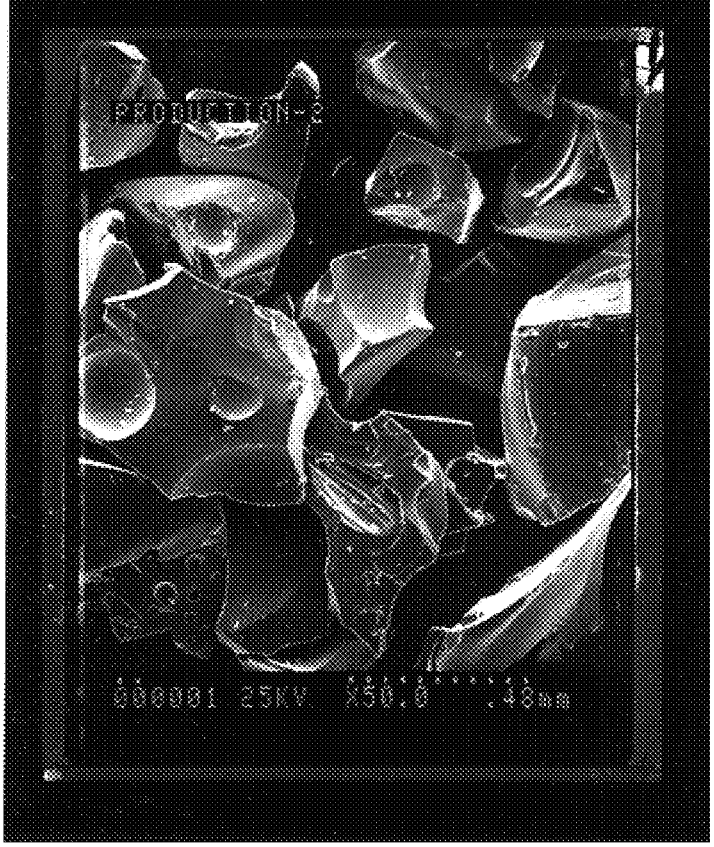
FIG. 3 is a 50 times enlarged electron micrograph of powders of the resin precursor (with a particle size ranging from 300 to 600 μm) in accordance with reference example 2 substituted for a drawing.

The water-soluble component in the resin precursor (A) was less than 10 percent. To the resin precursor (A), foams are not observed by an electric microscope. The BET specific surface area of the particles with a diameter of from 300 to 600 μm in the resin precursor (A) was 0.018 m²/g. An electron micrograph of the non-porous particles of the irregular shape (with a diameter of from 300 to 600 μm) in the resin precursor (A) is shown in FIG. 2. The properties thereof are summarized in Table 1.

TABLE 1

| WATER-ABSORBENT AGENT | TEMP OF POWDERS DURING THE PROCESS | ABSORBENCY (g/g) | ABSORBENCY UNDER PRESSURE (g/g) | RESIDUAL CROSS-LINKING AGENT (ppm) | ABSORBING RATE (g/g/sec) |
|---|---|---|---|---|---|
| RESIN PRECURSOR (A) | — | 44 | 11 | (NOT USED) | 0.31 |
| RESIN PRECURSOR (B) | — | 52 | 9 | (NOT USED) | 0.30 |
| RESIN PRECURSOR (C) | — | 45 | 8 | (NOT USED) | 0.72 |
| RESIN PRECURSOR (D) | — | 44 | 8 | (NOT USED) | 0.65 |

TABLE 1-continued

| WATER-ABSORBENT AGENT | TEMP OF POWDERS DURING THE PROCESS | ABSORBENCY (g/g) | ABSORBENCY UNDER PRESSURE (g/g) | RESIDUAL CROSS-LINKING AGENT (ppm) | ABSORBING RATE (g/g/sec) |
|---|---|---|---|---|---|
| WATER-ABSORBENT RESIN (1) | — | 40 | 22 | 130 | 0.22 |
| WATER-ABSORBENT RESIN (2) | — | 43 | 26 | 40 | 0.28 |
| WATER-ABSORBENT RESIN (3) | — | 38 | 24 | 70 | 0.70 |
| WATER-ABSORBENT RESIN (4) | — | 37 | 23 | 60 | 0.65 |
| WATER-ABSORBENT RESIN (5) | — | 30 | 15 | 3 | 0.30 |

REFERENCE EXAMPLE 2

As a monomer to be used in polymerization, to 5,500 g of a monomer solution of acrylate sodium salt that was 75 mole percent neutralized sodium salt acrylate (with a monomer density of 33 percent), 4.9 g (0.045 mole percent) of polyethylene glycol diacrylate (n=8) was dissolved as an inner crosslinking agent.

After the mixed solution was replaced with nitrogen, it was polymerized by leaving at rest with a thickness of around 5 cm in the following manner. 2.40 g of sodium persulfate and 0.12 g of L-ascorbic acid were added as a polymerization initiator, and further 4 g of 2,2'-azobis(2-amidinopropane) dihydrochloride which serves both as a foaming agent and a polymerization initiator was added to be uniformly dissolved therein. After an elapse of time of 1 minute, a polymerization was started. The mixed solution has a peak temperature reached to 70° C. in the polymerization reaction.

The resulting hydrogel polymer from the polymerization reaction was porous gel-like polymer containing foam with a diameter ranging from 1 to 2 mm. The hydrogel polymer was pulverized by a meat chopper, and was placed on a metal gauze of 300 μm and dried under hot air at 160° C. for 60 minutes. Then, the resulting dried polymer was pulverized by a roll mill and further classified by a metal gauze of 850 μm mesh to obtain a resin precursor (B). The resulting resin precursor (B) had an irregular shape, and an average particle diameter of 330 μm, the resin precursor (B) having a content a resin having a particle diameter of less than 150 μm of 8 percent by weight and a water content of 6 percent by weight.

The water-soluble component in the resin precursor (B) was less than 10 percent. The BET specific surface area of particles with a diameter ranging from 300 to 600 μm in the resin precursor (B) was 0.025 m²/g. The resin precursor (B) was observed with the electron microscope and was found to be porous in which foams are partially formed in the particles. An electron micrograph of the partially porous particles of the irregular shape (with a diameter of from 300 to 600 μm) in the resin precursor (B) is shown in FIG. 2. The properties thereof are summarized in Table 1.

REFERENCE EXAMPLE 3

While keeping the temperature of the solution at 20° C., to 36 parts of 10 percent concentration of 2,2'-azobis(2-methylpropionamizine) dihydrochloride solution, 6.7 parts of 37 percent solution of sodium acrylate were added with stirring at 1200 rpm to form a mixed solution. After an elapse of time of several seconds, the mixed solution was turbid, thereby obtaining a white solid portion in a form of fine particles with an average diameter of 10 μm.

By filtering off the white turbid solution, around 2.2 parts of white solid portion of fine particles with an average particle diameter of 10 μm were isolated, and were rinsed off with water to be purified. The solid portion was confirmed with UV absorption (365 nm) showing a particular azo group, and based on the results of element analysis, it was found that the resulting solid was 2,2'-azobis(2-methylpropionamizine) diacrylate having a uniform water dispersibility.

In the polymerization device to be used in Example 2, as a monomer for use in polymerization, to 5500 g (with a monomer content of 38 percent) of 75 mole percent neutralized acrylate sodium salt, 3.49 g (0.05 mole percent) trimethylolpropane triacrylate was dissolved as an inner crosslinking agent, and 4 g of 2,2'-azobis(2-methylpropionamizine) diacrylate complex was uniformly dispersed as the foaming agent. Then, sodium persulfate and L-ascorbic acid were added in the same manner as Reference 2.

In the resulting hydrogel polymer, foam (bubbles) with a diameter of not more than 100 μm was uniformly contained. The hydrogel polymer is a porous gel-like polymer which is white in color due to the resulting foam (bubbles). The hydrogel polymer was cut into pieces of from 5 to 10 mm, and was placed on a metal gauze with 300 μm (50 mesh), and was dried for 60 minutes at 150° C. The dried product was pulverized by a roll mill and further classified by a metal gauze of 850 μm mesh, thereby obtaining a resin precursor (C).

The resin precursor (C) has an irregular crushed shape with an average particle diameter of 300 μm, and a ratio of the resin having a particle diameter of less than 150 μm of 8 percent by weight and a water content of 6 percent by weight.

Figure 4:
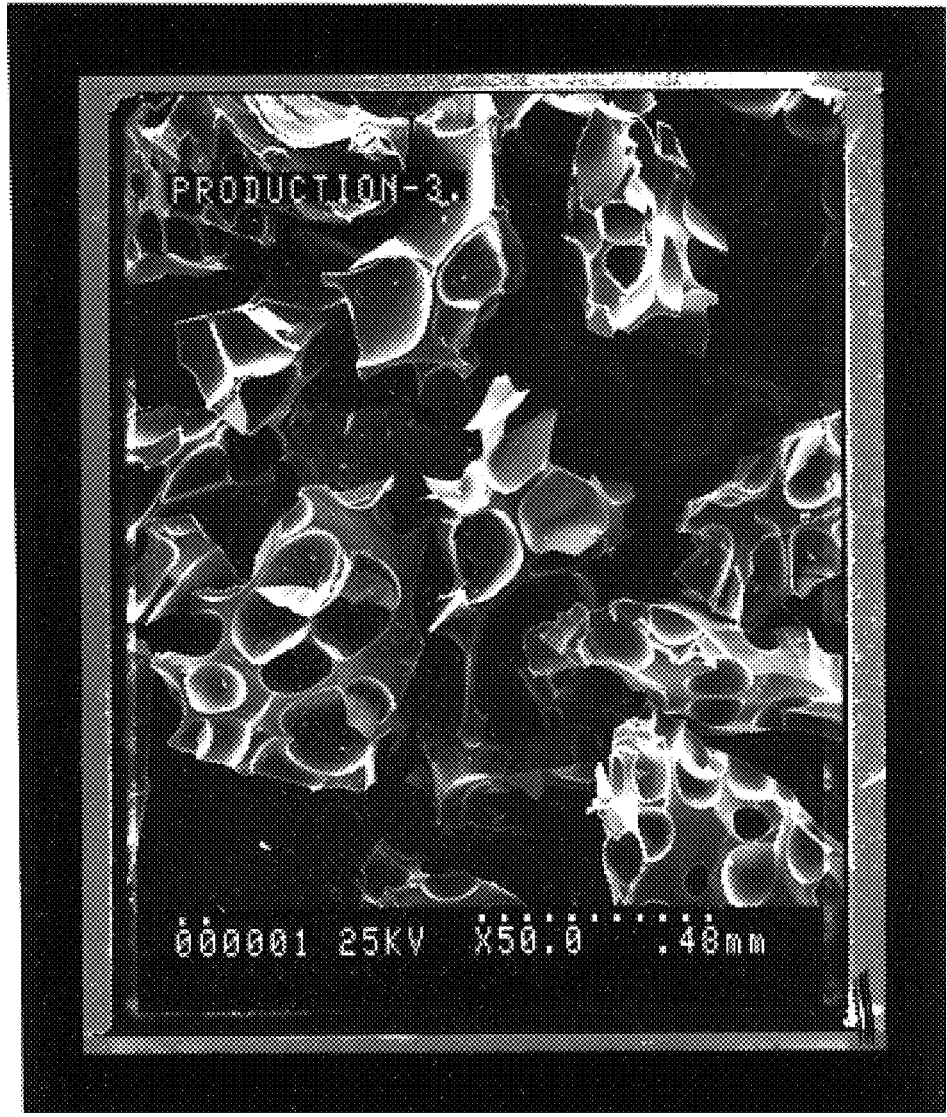
FIG. 4 is a 50 times enlarged electron micrograph of powders of the resin precursor (with a particle size ranging from 300 to 600 μm) in accordance with reference example 3 substituted for a drawing.

The water-soluble content of the resin precursor (C) was less than 10 percent. In the resin precursor (C), the BET specific surface area with a particle of from 300 to 600 μm was 0.04 m²/g. The resin precursor (C) was observed by the electron microscope, and was found to be porous in which foam (bubbles) is uniformly formed in the particle. An electron micrograph which shows the particle structure of the porous irregular crushed type (with a diameter of from 300 to 600 μm) shown in FIG. 4. The properties thereof are summarized in Table 1.

REFERENCE EXAMPLE 4

Reference example 3 was repeated except that the foaming agent was changed to 50 g of sodium carbonate, and 2 g of polyoxyethylene sorbitan monostearate and 10 g of hydroxy ethyl cellulose were used as an auxiliary material of the foaming agent with respect to the monomer solution to uniformly disperse the foaming agent to the monomer solution.

The monomer solution was polymerized in the same manner as Example 3. The resulting hydrogel polymer was porous gel-like polymer which was white in color as foam (bubbles) with a particle diameter of not more than 100 μm were uniformly formed. The hydrogel polymer was cut into pieces of from around 5 to 10 mm, and was dried, pulverized, and was classified like Example 3, and the resin precursor (D) was obtained.

The resin precursor (D) had an irregular shape having a content of particles with an average particle diameter of 360 μm and a content of the particles of particle diameter of less than 150 μm of 8 percent by weight and water content of 6 percent by weight. The water-soluble component of the resin precursor (D) was less than 10 percent. In the resin precursor (D), the BET specific surface area of particles with a particle diameter of from 300 to 600 μm was 0.03 m²/g. The resin precursor (D) was observed with the electron microscope and was found to be porous in which foams are uniformly formed entirely. The properties of the resin precursor (D) are summarized in Table 1.

COMPARATIVE EXAMPLE 1

To 100 parts of the non-porous resin precursor (A) resulting from Reference Example 1, 0.1 parts of ethylene glycol diglycidyl ether as a crosslinking agent with an epoxy group and 4 parts of water were mixed, and a heat treatment was applied to the mixture for 40 minutes at 120° C., thereby obtaining the water-absorbent resin powders (1). The properties thereof were summarized in Table 1.

COMPARATIVE EXAMPLE 2

To 100 parts of the resin precursor (B) resulting from Reference Example 2, which was partially porous, 0.1 part of ethylene glycol diglycidyl ether as a crosslinking agent with an epoxy group, 4 parts of water and 0.5 parts of isopropyl alcohol were mixed, and a heat treatment was applied to the mixture for 30 minutes at 120° C., thereby obtaining the water-absorbent resin powders (2). The properties thereof are summarized in Table 1.

COMPARATIVE EXAMPLE 3

To 100 parts of the resin precursor (C) resulting from Reference Example 3, which was homogeneously porous, a solution of a crosslinking agent composed of 0.15 part of ethylene glycol diglycidyl ether as a crosslinking agent with an epoxy group, 4 parts of water and 1 part of ethyl alcohol were mixed, and a heat treatment was applied to the mixture for 30 minutes at 180° C., thereby obtaining the water-absorbent resin powders (3). The properties thereof are summarized in Table 1.

COMPARATIVE EXAMPLE 4

To 100 parts of the resin precursor (D) resulting from Reference Example 4, which was homogeneously porous, a solution of a crosslinking agent composed of 0.15 part of ethylene glycol diglycidyl ether having an epoxy group, 4 parts of water and 1 part of ethyl alcohol were mixed, and the mixture was heated for 40 minutes at 120° C., thereby obtaining the water-absorbent resin powders (4). The properties thereof are summarized in Table 1.

COMPARATIVE EXAMPLE 5

In order to reduce the amount of a residue of the crosslinking agent, the amount of the crosslinking agent having an epoxy group was reduced, and an amount of water was increased on the contrary. Namely, to 100 parts of non-porous resin precursor (A) resulting from reference example 1, a solution of the crosslinking agent composed of 0.01 parts of ethylene glycol diglycidyl ether and 40 parts of water, and 10 parts of isopropanol was mixed. Then, a heat treatment was applied to the resulting mixture at 120° C. for 40 minutes, thereby obtaining the water-absorbent resin powders (5). As summarized in Table 1, the resulting water-soluble resin powders (5) were inferior in their properties, especially absorbency under high pressure when the amount of a residue of crosslinking agent after the surface-crosslinkage was small as shown in Table 1.

EXAMPLE 1

100 parts of the water-absorbent resin powders (1) resulting from comparative example 1, while keeping the temperature of the powders at 50° C., were mixed with 5 parts of 30 percent polyethylene imine solution (epomine P-1000 available from Nippon Shokubai, Co Ltd.) as a nucleophilic reagent to be absorbed therein and the mixture was heated at 40° C. for 30 minutes in a form of powders, and then the product sized by passing a metal gauze of 20 mesh (850 μm) was taken out, thus obtaining the water-absorbent agent powders (1) of this invention. The resulting water-absorbent agent powders (1) had an absorbency without pressure of 38 g/g and an absorbency under an applied high pressure of 21 g/g and the amount of residual crosslinking agent (ethylene glycol diglycidyl ether) of 1 ppm. The respective properties thereof are summarized in Table 2.

TABLE 2

| WATER-ABSORBENT AGENT POWDERS | TEMP OF POWDERS DURING THE PROCESS (° C.) | ABSORBENCY (g/g) | ABSORBENCY UNDER PRESSURE (g/g) | RESIDUAL CROSS-LINKING AGENT (ppm) | ABSORBING RATE (g/g/sec) |
|---|---|---|---|---|---|
| POWDERS (1) | 50 | 38 | 21 | 1 | 0.22 |
| POWDERS (2) | 50 | 41 | 22 | ND | 0.24 |

TABLE 2-continued

| WATER-ABSORBENT AGENT POWDERS | TEMP OF POWDERS DURING THE PROCESS (° C.) | ABSORBENCY (g/g) | ABSORBENCY UNDER PRESSURE (g/g) | RESIDUAL CROSS-LINKING AGENT (ppm) | ABSORBING RATE (g/g/sec) |
|---|---|---|---|---|---|
| POWDERS (3) | 40 | 42 | 21 | ND | 0.22 |
| POWDERS (4) | 60 | 43 | 26 | 6 | 0.31 |
| POWDERS (5) | 60 | 43 | 26 | 2 | 0.32 |
| POWDERS (6) | 60 | 43 | 25 | 1 | 0.31 |
| POWDERS (7) | 70 | 37 | 23 | 7 | 0.66 |
| POWDERS (8) | 40 | 35 | 21 | 10 | 0.65 |
| POWDERS (9) | 40 | 32 | 20 | 7 | 0.60 |
| POWDERS (10) | 40 | 43 | 26 | 4 | 0.40 |
| POWDERS (11) | 90 | 43 | 24 | 2 | 0.30 |
| POWDERS (12) | 130 | 43 | 23 | 4 | 0.29 |
| POWDERS (13) | 45 | 38 | 24 | 5 | 0.74 |
| POWDERS (14) | 45 | 37 | 23 | ND | 0.84 |
| POWDERS (15) | 45 | 37 | 23 | ND | 0.88 |
| POWDERS (16) | 45 | 37 | 23 | 2 | 0.70 |
| POWDERS (17) | 30 | 35 | 22 | 8 | 0.71 |
| COMPARATIVE POWDERS (6) | 20 | 43 | 21 | 15 | 0.30 |
| COMPARATIVE POWDERS (7) | 40 | 44 | 10 | 1 | 0.25 | powder: water-absorbent agent powder

In Table 2, ND indicates below detectable limit.

EXAMPLE 2

Example 1 was repeated except that 5 parts of 30 percent sodium bisulfite solution was used as a nucleophilic reagent in place of the 30 percent polyethylene imine solution to obtain water-absorbent agent powders (2). The water-absorbent agent powders (2) showed absorbency without pressure of 41 g/g, and an absorbency under high pressure of 22 g/g, in which the residual ethyleneglycol diglycidyl ether was not detected. The properties thereof were summarized in Table 1.

EXAMPLE 3

100 g of the water-absorbent resin powders (1) resulting from comparative example 1 was washed by contacting with 1,000 cc mixed solution of water and ethyl alcohol with a weight ratio of 50:50 with stirring for 30 minutes while keeping the temperature of the powders at 40° C., and thereafter the resulting mixture was filtered off and was dried under reduced pressure for 24 hours at 50° C., thereby obtaining the water-absorbent agent powders (3) of the present invention. The resulting water-absorbent agent powders (3) showed absorbency without pressure of 42 g/g and the absorbency under high pressure of 21 g/g, and the residual ethyleneglycol diglycidyl ether was not detected. The result of respective properties are shown in Table 2.

EXAMPLE 4

To 100 parts of water-absorbent resin powders (2) resulting from comparative example 2 while maintaining its temperature at 60° C., 3 parts of water was added as the nucleophilic reagent to be absorbed therein. Thereafter, the resulting mixture was dried at 80° C. for 1 hour, and was passed through a gauze of JIS standard of 850 μm, thereby obtaining the water-absorbent agent powders (4). The properties of the water-absorbent agent powders (4) are shown in Table 2.

EXAMPLE 5

Example 4 was repeated except that 2 parts by weight of water was further added, i.e., the total amount of water to be added as the nucleophilic reagent was 5 parts, thereby obtaining water-absorbent agent powders (5). The water-absorbent agent powders (5) showed properties summarized in Table 2.

EXAMPLE 6

Example 4 was repeated except that 10 parts of water were added as the nucleophilic reagent in total, thereby obtaining water-absorbent agent powders (6). The water-absorbent agent powders (6) showed properties summarized in Table 2.

EXAMPLE 7

To 100 parts by weight of water-absorbent resin powders (3) resulting from comparative example 3, while keeping the temperature of the powders at 70° C. in a form of powder, 3 parts of diethanol amine (nucleophilic reagent) were added to be absorbed therein. The resulting mixture was heated for 1 hour at 60° C. in a form of powder, and then the mixture was passed through a metal gauze of 850 μm, thereby obtaining the water-absorbent agent powders (7). The resulting water-absorbent agent powders (7) showed properties summarized in Table 2.

EXAMPLE 8

To 100 parts by weight of water-absorbent resin powders (4) resulting from comparative example 4, while keeping the temperature of the powders at 40° C., 5 parts of propylene glycol (nucleophilic reagent) were added therein. The resulting mixture was heated in a form of powder for 1 hour at 80° C., and then the mixture was passed through a metal gauze of 850 μm, thereby obtaining the water-absorbent agent powders (8). The resulting water-absorbent agent powders (8) showed properties summarized in Table 2.

EXAMPLE 9

Example 8 was repeated except that an amount of propylene glycol (nucleophilic reagent) was altered to 15 parts, thereby obtaining water-absorbent agent powders (9). The resulting water-absorbent agent powders had properties shown in Table 2.

EXAMPLE 10

Example 4 was repeated except that 0.1 part of nonionic surfactant agent polyoxyethylene sorbitan monostearate (HLB=14.9) and 5 parts of water (nucleophilic reagent) were added, and subsequently, a heat treatment was applied for 1 hour at 60° C. while maintaining the solid portion, and then dried, thus obtaining a water-absorbent agent powders (10). The resulting water-absorbent agent powders (10) had properties shown in Table 2.

COMPARATIVE EXAMPLE 6

Example 6 was repeated except that the temperature of the water-absorbent resin powders (2) to which the nucleophilic reagent was to be added was changed from 60° C. (Example 6) to 20° C. to obtain comparative water-absorbent agent powders (6). In this comparative example, the nucleophilic reagent was continuously mixed with the water-absorbent resin powders, and a cohered lump was formed in the resin to be supplied gradually, resulting in non-uniform mixture. The properties of the final product of the comparative water-absorbent agent powders (6) are shown in Table 2. Compared with the water-absorbent agent powders (6) resulting from example 6, the comparative water-absorbent agent powders (6) showed apparently a larger amount of agglomeration, and inferior properties.

COMPARATIVE EXAMPLE 7

Example 6 in which processes were carried out in form of powder was repeated except that the amount of additive (nucleophilic reagent) was set to 100 parts. Then, in the same manner as Example 6, water-absorbent resin powders (2) were processed in a gel state, and were passed through by a gauze of 850 μm after applying a heat treatment, thereby obtaining comparative water-absorbent agent powders (7). The resulting comparative water-absorbent agent powders (7) had properties shown in Table 2. The comparative water-absorbent agent powders (7) showed substantially the same effect of reducing the amount of a residue of the crosslinking agent; however, the absorbency thereof under pressure was greatly lowered.

EXAMPLE 11

Example 6 was repeated except that the temperature of the water-absorbent resin powders (2) to which the nucleophilic reagent was to be added was changed from 60° C. (Example 6) to 90° C. to obtain water-absorbent agent powders (11). The mixability of the nucleophilic reagent to the water-absorbent resin powders was significantly superior to that of comparative Example 5 at 20° C. but slightly inferior to that of example 6 in which the process was carried out at 60° C. The resulting water-absorbent agent powders (11) were slightly inferior in its absorbency under high pressure and the effect of reducing the residual crosslinking agent to those of example 6.

EXAMPLE 12

Example 6 was repeated except that the temperature of the water-absorbent resin powders to which the nucleophilic reagent was to be added was changed from 60° C. (Example 6) to 130° C. to obtain water-absorbent agent powders (12). The mixability of the nucleophilic reagent to the water-absorbent resin powders was significantly superior to that of comparative example 5, but slightly inferior to that of example 11 in which the process was carried out at 90° C. The resulting water-absorbent agent powders (12) had properties shown in Table 2. The water-absorbent agent powders (12) were slightly inferior in its absorbency under high pressure and the effect of reducing the. residual crosslinking agent to those of example 6.

EXAMPLE 13

To 100 parts by weight of water-absorbent resin powders (3) resulting from comparative example 3, while keeping the temperature of the powders at 45° C., 8 parts of water (nucleophilic reagent) were added to be absorbed therein. Then, while keeping the solid portion, the mixture was further heated for 1 hour at 60° C. in a form of powder, and then dried, and was passed through a metal gauze of 850 μm, thereby obtaining the water-absorbent agent powders (13). The respective properties of the water-absorbent agent powders (13) were shown in Table 2.

EXAMPLE 14

Example 13 was repeated except that 0.1 part of polyoxyethylene sorbitan monostearate (HLB=14.9) as nonionic surfactant and 8 parts of water as nucleophilic reagent were added as nucleophilic reagent, further 1 part of triethanol amine was used, thereby obtaining water-absorbent agent powders (14). The resulting water-absorbent agent powders (14) showed properties summarized in Table 2.

EXAMPLE 15

Example 13 was repeated except that 0.1 parts of polyoxyethylene sorbitan monostearate (HLB=14.9) as a nonionic surfactant and 8 parts of water as a nucleophilic reagent were added. Further, 3 parts of urea were used, thereby obtaining water-absorbent agent powders (15). The resulting water-absorbent agent powders (15) had properties summarized in Table 2.

EXAMPLE 16

Example 13 was repeated except that in addition to 8 parts of water as a nucleophilic reagent, 2 parts of sodium hydroxide were used, and further 0.1 part of sodium polyoxyethylene lauryl ether sulfonate as a surfactant were added, thereby obtaining water-absorbent agent powders (16). The resulting water-absorbent agent powders (16) showed properties summarized in Table 2.

EXAMPLE 17

To 100 parts of water-absorbent resin powders (3) obtained from comparative example 3 maintained at 30° C., 8 parts of water were absorbed under temperature of 30° C. and humidity of 90% RH. Next, the resulting mixture was sealed and left in a form of powder for 40 days without an application of heat, thereby obtaining the water-absorbent agent powders (17). The water-absorbent agent powders (17) showed properties summarized in Table 2.

INDUSTRIAL APPLICATIONS OF THE PRESENT INVENTION

The manufacturing method of water-absorbent agent powders of the present invention in which to conventional surface crosslinked water-absorbent resin powders in a form of powder under an applied heat, a nucleophilic reagent is added to reduce an amount of a residue of a crosslinking agent, offers water-absorbent agent powders which show as high absorbency under high pressure as without pressure without having a residue of a crosslinking agent containing a highly reactive epoxy group in the water-absorbent agent powders with ease and stably. The water-absorbent agent powders of the present invention manifest a high absorbing rate, liquid permeability and are not likely to be moved or separated from a pulp. Having the described beneficial properties, the water-absorbent agent powders of the present invention are suited for use in especially sanitary materials such as disposable diapers, sanitary napkins, etc.

The water-absorbent agent powders of the present invention show as high absorbency under high pressure as without pressure without having a residue of a crosslinking agent of a highly reactive epoxy group, high absorbing rate, high permeability of liquid, and are not likely to be shifted or fallen off from pulp. Such water-absorbent agent powders are suited for use in sanitary material such as disposable diaper, sanitary napkins, etc.

What is claimed is:

1. A manufacturing method of a water-absorbent agent powder from a water-absorbent resin powder having a carboxyl group in which surface regions are crosslinked by a crosslinking agent having an epoxy group, characterized by comprising the step of:

adding a nucleophilic reagent to heated said water-absorbent resin powder in a form of powder, and having a residue of the cross-linking agent remaining therein so as to reduce an amount of the residue of the cross-linking agent.

2. The manufacturing method as set forth in claim 1, characterized in that:

an absorbency under pressure based on a physiologic saline solution under load of 50 g/cm$^2$ of the water-absorbent resin powder is not less than 20 g/g.

3. The manufacturing method as set forth in claim 1, characterized in that:

the water-absorbent resin powder has an irregular crushed shape resulting from carrying out a solution polymerization of a water-soluble unsaturated monomer and further pulverizing the polymer.

4. The manufacturing method as set forth in claim 1, characterized in that:

the water-absorbent resin powders are porous and is obtained in a presence of a foaming agent.

5. The manufacturing method as set forth in claim 4, characterized in that:

said foaming agent is at least one member selected from the group consisting of a water-soluble azo compound and carbonate.

6. The manufacturing method as set forth in claim 1, characterized in that:

a BET specific surface area of the water-absorbent resin powder before being surface crosslinked is not less than 0.025 m$^2$/g, with respect to said water-absorbent resin powders having a particle diameter in a range of from 300 to 600 μm.

7. The manufacturing method as set forth in claim 1, characterized in that:

surface regions of said water-absorbent resin powder are crosslinked by adding a solution containing from 0.005 to 2 parts by weight of said crosslinked agent having an epoxy group and from 0.1 to 10 parts by weight of water based on 100 parts by weight of a hydrophilic crosslinked polymer dried to a water content of less than 10 percent.

8. The manufacturing method as set forth in claim 1, characterized in that:

an amount of the residue of the crosslinking agent having an epoxy group is in a range of from 2 to 2,000 ppm.

9. The manufacturing method as set forth in claim 1, characterized in that:

said nucleophilic reagent is a liquid.

10. The manufacturing method as set forth in claim 9, characterized in that:

said nucleophilic reagent is water.

11. The manufacturing method as set forth in claim 9, characterized in that:

said nucleophilic reagent is used in an amount of from 1 to 30 parts by weight based on 100 parts by weight of the water-absorbent resin powder.

12. The manufacturing method as set forth in claim 9, characterized in that:

said nucleophilic reagent has a pH value of not less than 5.

13. The manufacturing method as set forth in claim 9, characterized in that:

a nucleophilic atom of said nucleophilic reagent is at least one member selected from the group consisting of nitrogen and sulfur.

14. The manufacturing method as set forth in claim 1, characterized in that:

at least two kinds selected from the group consisting of water and nucleophilic reagents having a nucleophilic atom of nitrogen and/or sulfur are used simultaneously in combination as said nucleophilic reagent.

15. The manufacturing method as set forth in claim 13, characterized in that:

said nucleophilic reagent is at least one member selected from the group consisting of amine, ammonia, ammonium carbonate, sulfurous acid (sulfite), hydrogensulfuric acid (hydrogensulfite), thiosulfuric acid (thiosulfate), urea, thiourea, and amide.

16. The manufacturing method as set forth in claim 13, characterized in that:

said nucleophilic reagent is polyamine and/or hydrogensulfite.

17. The manufacturing method as set forth in claim 1, characterized by further comprising the step of:

adding a water-soluble surfactant.

18. The manufacturing method as set forth in claim 9, characterized in that:

said water-absorbent resin powder is heated in a presence of said nucleophilic reagent.

19. The manufacturing method as set forth in claim 18, characterized in that:

said water-absorbent resin powder is heated for at least 10 minutes in a presence of said nucleophilic reagent.

20. The manufacturing method as set forth in claim 18, characterized in that:

a heat-treatment is applied in such a manner that a temperature of said water-absorbent resin powder is set such that said nucleophilic reagent is made at least partially in contact therewith in a vapor state.

21. The manufacturing method as set forth in claim 1, characterized in that:

said heated water-absorbent resin powder has a temperature ranging from 30 to 100° C.

22. The manufacturing method as set forth in claim 1, characterized in that:

an absorbing rate (g/g/sec) after said nucleophilic reagent treatment is applied is higher than that before the nucleophilic reagent treatment is applied.

23. The manufacturing method as set forth in claim 1, characterized in that:

an amount of the crosslinking agent having an epoxy group is reduced to not more than 2 ppm after the nucleophilic reagent treatment is applied, while keeping the absorbency under pressure to be not less than 20 g/g.

24. The manufacturing method as set forth in claim 18, characterized in that:

said nucleophilic reagent is absorbed in said water-absorbent resin powder.

25. The manufacturing method as set forth in claim 1, characterized in that:

said nucleophilic reagent is divided to be added repetitively.

26. A manufacturing method of a water-absorbent agent powder, characterized by comprising the step of:

washing a water-absorbent resin powder having a carboxyl group in which surface regions are crosslinked by a crosslinking agent having an epoxy group, and a residue of the crosslinking agent remains therein so as to reduce an amount of the residue of said crosslinking agent.

27. The manufacturing method as set forth in claim 26, characterized in that:

a washing treatment is carried out by contacting a water-absorbent resin with a mixed solution composed of water and hydrophilic organic solvent, and subsequently separating the mixed solution from said water-absorbent resin.

28. The manufacturing method as set forth in claim 26, characterized in that:

the mixed solution is selected so as to prevent said water-absorbent resin powder from swelling.

29. The manufacturing method as set forth in claim 26, characterized in that:

an absorbency under pressure based on a physiologic saline solution under load of 50 g/cm² of the water-absorbent resin powder is not less than 20 g/g.

30. The manufacturing method as set forth in claim 26, wherein:

said water-absorbent resin powder is porous and is obtained in a presence of a foaming agent.

31. The manufacturing method as set forth in claim 26, characterized in that:

the water-absorbing resin powder has an irregular shape resulting from carrying out a solution polymerization of a water-soluble unsaturated monomer and further pulverizing the polymer.

32. The manufacturing method as set forth in claim 30, characterized in that:

said foaming agent is at least one member selected from the group consisting of a water-soluble azo compound and carbonate.

33. The manufacturing method as set forth in claim 26, characterized in that:

a BET specific surface area of the water-absorbent resin powder before being surface crosslinked is not less than 0.025 m²/g, with respect to said water-absorbent resin powder having a particle diameter in a range of from 300 to 600 μm.

34. The manufacturing method as set forth in claim 26, characterized in that:

surface regions of said water-absorbent resin powder are crosslinked by adding a solution containing from 0.005 to 2 parts by weight of said crosslinking agent having an epoxy group and from 0.1 to 10 parts by weight of water based on 100 parts by weight of a hydrophilic crosslinked polymer dried to a water content of less than 10 percent.

35. The manufacturing method as set forth in claim 26, characterized in that:

an amount of the residue of said crosslinking agent having an epoxy group is in a range of from 2 to 2,000 ppm in the water-absorbent resin powder prior to washing.

36. A manufacturing method of a water-absorbent agent powder from dried water-absorbent resin powder of an irregular shape having a carboxyl group in which surface regions are crosslinked by a crosslinking agent having an epoxy group, said water-absorbent resin powder having an absorbency under pressure based on physiologic saline solution under a load of 50 g/cm² increased to 20 g/g due to the surface region crosslinkage:

adding at least one member selected from the group consisting of a water-soluble surfactant and a water-soluble polymer to said water-absorbent resin powder in a sufficient amount for increasing an absorbing rate (g/g/sec) of said water-absorbent resin powder defined based on 28 times swollen with artificial urine above an absorbing rate of said surface crosslinked water-absorbent resin powder.

37. A manufacturing method of a water-absorbent agent powder, characterized by comprising the step of:

adding water to water-absorbent resin powder being at least partially porous, having a carboxyl group, said water-absorbent resin powder being surface crosslinked by a crosslinking agent having an epoxy group and containing a residual surface crosslinking agent having the epoxy group so as to have an absorbency under pressure of not less than 20 g/g based on a physiologic saline solution under load of 50 g/cm², whereby an amount of the residue of the crosslinking agent is reduced from a mixture in a form of powder.

38. The manufacturing method as set forth in claim 37, characterized by heat-treating the mixture in a form of powder.

39. The manufacturing method of the present invention as set forth in claim 37, characterized in that:

a process is carried out by leaving the mixture in a form of powder for not less than 10 days at room temperature.

40. Water-absorbent agent powder, characterized by comprising:

at least partially porous water-absorbent resin powder, wherein:

said water-absorbent resin powder is crosslinked by a crosslinking agent having an epoxy group, and an amount of a residue of the crosslinking agent is not more than 2 ppm.

41. The water-absorbent agent powder as set forth in claim 40, characterized in that:

an absorbency under load of 50 g/cm² with respect to a physiologic saline solution is not less than 20 g/g.

42. The water-absorbent agent powder as set forth in claim 40, characterized in that:

a BET specific surface area of a hydrophilic resin crosslinking material before surface regions thereof are crosslinked, which is a resin precursor of water-absorbent resin powders, is not less than 0.025 m²/g with respect to said resin precursor having a particle diameter ranging from 300 to 600 µm.

43. The water-absorbent agent powder as set forth in claim 40, characterized in that:

an absorbing rate defined based on 28 times swollen with artificial urine is not less than 0.7 g/g/sec.

* * * * *